US011051718B2

(12) United States Patent
An et al.

(10) Patent No.: US 11,051,718 B2
(45) Date of Patent: Jul. 6, 2021

(54) SYSTEMS AND METHODS FOR MANAGING HEART FAILURE USING HEART SOUNDS

(71) Applicant: Cardiac Pacemakers, Inc., St. Paul, MN (US)

(72) Inventors: Qi An, Blaine, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 254 days.

(21) Appl. No.: 15/992,531

(22) Filed: May 30, 2018

(65) Prior Publication Data
US 2018/0344212 A1 Dec. 6, 2018

Related U.S. Application Data

(60) Provisional application No. 62/513,603, filed on Jun. 1, 2017.

(51) Int. Cl.
*A61B 5/11* (2006.01)
*A61N 1/362* (2006.01)
(Continued)

(52) U.S. Cl.
CPC .......... *A61B 5/1102* (2013.01); *A61B 5/0022* (2013.01); *A61B 5/0205* (2013.01);
(Continued)

(58) Field of Classification Search
CPC ....... A61B 7/04; A61B 5/0205; A61B 5/0402; A61B 5/0452
See application file for complete search history.

(56) References Cited

U.S. PATENT DOCUMENTS 6,726,635 B1 * 4/2004 LaSala ............... A61B 7/04
181/131
7,853,327 B2 12/2010 Patangay et al.
(Continued)

FOREIGN PATENT DOCUMENTS

| CN | 111065435 A | 4/2020 |
| WO | WO-2018031906 A1 | 2/2018 |
| WO | WO-2018222651 A1 | 12/2018 |

OTHER PUBLICATIONS

"European Application Serial No. 18733061.8, Response to Communication Pursuant to Rules 161 and 162 filed Jul. 15, 2020", 12 pgs.
(Continued)

*Primary Examiner* — Michael J D Abreu
(74) *Attorney, Agent, or Firm* — Schwegman Lundberg & Woessner, P.A.

(57) ABSTRACT

Systems and methods for monitoring and treating patients with heart failure are described. A signal receiver may receive a heart sound (HS) signal and an impedance signal sensed from the patient. A heart sound detector circuit may use at least the received impedance signal to determine a HS detection window, and detect a HS component indicative of cardiac diastolic function from the received HS signal within the HS detection window. The system may include a heart failure detector circuit that may generate a cardiac diastolic function indicator (DFI) using the detected HS component and, in certain examples, may detect worsening heart failure using the generated DFI. The system may include a therapy circuit to deliver or adjust an electrostimulation therapy based on DFI.

20 Claims, 9 Drawing Sheets

(51) Int. Cl.
*A61B 5/053* (2021.01)
*A61N 1/365* (2006.01)
*A61B 5/00* (2006.01)
*A61B 7/04* (2006.01)
*A61B 5/02* (2006.01)
*A61B 5/029* (2006.01)
*A61B 5/024* (2006.01)
*A61B 5/0205* (2006.01)
*A61N 1/375* (2006.01)
*A61N 1/372* (2006.01)
*A61B 5/349* (2021.01)
*G16H 10/60* (2018.01)

(52) U.S. Cl.
CPC .......... *A61B 5/029* (2013.01); *A61B 5/02028* (2013.01); *A61B 5/02438* (2013.01); *A61B 5/053* (2013.01); *A61B 5/4836* (2013.01); *A61B 7/04* (2013.01); *A61N 1/3627* (2013.01); *A61N 1/36578* (2013.01); *A61B 5/024* (2013.01); *A61B 5/1116* (2013.01); *A61B 5/349* (2021.01); *A61B 5/7264* (2013.01); *A61N 1/365* (2013.01); *A61N 1/3756* (2013.01); *A61N 1/37282* (2013.01); *G16H 10/60* (2018.01)

(56) References Cited

U.S. PATENT DOCUMENTS

| | | |
|---|---|---|
| 9,375,152 B2 | 6/2016 | An et al. |
| 2005/0149136 A1* | 7/2005 | Siejko ............ A61B 7/00 607/17 |
| 2006/0253300 A1 | 11/2006 | Somberg et al. |
| 2006/0282000 A1 | 12/2006 | Zhang et al. |
| 2008/0004904 A1* | 1/2008 | Tran ............ A61B 5/4818 705/2 |
| 2010/0063840 A1 | 3/2010 | Hoyme et al. |
| 2010/0069768 A1 | 3/2010 | Min et al. |
| 2013/0237773 A1 | 9/2013 | An et al. |
| 2015/0126883 A1 | 5/2015 | An et al. |
| 2015/0202443 A1* | 7/2015 | Zielinski ............ A61N 1/3684 607/18 |
| 2016/0051823 A1 | 2/2016 | Maile et al. |
| 2016/0331977 A1 | 11/2016 | Hettrick et al. |

OTHER PUBLICATIONS

"International Application Serial No. PCT/US2018/035023, International Preliminary Report on Patentability dated Dec. 12, 2019", 7 pgs.

"International Application Serial No. PCT/US2018/035023, International Search Report dated Sep. 19, 2018", 4 pgs.

"International Application Serial No. PCT/US2018/035023, Written Opinion dated Sep. 19, 2018", 5 pgs.

* cited by examiner

SYSTEMS AND METHODS FOR MANAGING HEART FAILURE USING HEART SOUNDS

CLAIM OF PRIORITY

This application claims the benefit of priority under 35 U.S.C. § 119(e) of U.S. Provisional Patent Application Ser. No. 62/513,603, filed on Jun. 1, 2017, which is herein incorporated by reference in its entirety.

TECHNICAL FIELD

This document relates generally to medical devices, and more particularly, to systems and methods for monitoring patients with a heart failure.

BACKGROUND

Congestive heart failure (CHF) is a leading cause of death in the United States and globally. CHF occurs when the heart is unable to adequately supply enough blood to maintain a healthy physiological state. CHF may be treated by drug therapy, or by an implantable medical device (IMD) such as for providing electrostimulation therapy.

Some IMDs may be used to monitor CHF patients and detect events leading to worsening of heart failure. The IMDs may include sensors to sense physiological signals from a patient. Frequent patient monitoring may help reduce heart failure hospitalization. Identification of patient at an elevated risk of developing future heart failure events, such as a heart failure decompensation event, may help ensure timely treatment and improve prognosis and patient outcome. Identifying and safely managing the patients having risk of future heart failure events can avoid unnecessary medical interventions, hospitalization, and thereby reduce healthcare cost.

Some IMDs may chronically stimulate excitable tissues or organs, such as a heart, to help restore or improve cardiac performance in a patient with CHF, or to treat abnormal cardiac rhythms. One example of electrostimulation therapy is resynchronization therapy (CRT) that may correct cardiac dyssynchrony. An IMD may have an electronics unit such as a pulse generator that generates and delivers electrostimulation to the heart or other target tissue.

SUMMARY

An ambulatory medical device (AMD), such as an implantable medical device, a subcutaneous medical device, a wearable medical device, or other external medical device, may be used to monitor heart failure (HF) patient, detect worsening heart failure (WHF), and deliver a therapy to restore or improve the cardiac function. The AMD may include implanted leads such as transvenous leads that include electrodes for cardiac sensing or for therapy delivery. The AMD may include physiological sensors to sense electrical or mechanical activities of the heart. The sensed physiological signals may be used to trigger delivery of a therapy, to assess therapy efficacy, or to adjust a therapy.

An AMD may include sensors to sense heart sounds, which may provide information about cardiac systolic and diastolic function. Systole is the contraction or a period of contraction of the heart that causes blood to be forced out of the heart such as the ventricles and into the aorta and pulmonary artery. Diastole is the relaxation or a period of relaxation of the heart during which the blood flows back into the heart such as the ventricles. Heart sounds are associated with mechanical vibrations of the heart and the blood flow through the heart. Heart sounds recur with each cardiac cycle and are separated and classified according to the activity associated with the vibration. Typically, heart sounds sensed from a subject may include several components within a cardiac cycle, including a first (S1), a second (S2), a third (S3), or a fourth (S4) heart sound. S1 is associated with the vibrational sound made by the heart during tensing of the mitral valve. S2 is produced by closure of the aortic and pulmonary valves, and marks the beginning of diastole. S3 is an early diastolic sound corresponding to passive ventricular filling during diastole, when the blood rushes into the ventricles. S4 is a late diastolic sound corresponding to active ventricular filling when the atria contract and push the blood into the ventricles. In a healthy subject, S3 is usually faint and S4 is rarely audible. However, a pathologic S3 or S4 may be higher pitched and louder.

Monitoring heart sounds may be useful to assess heart failure status. Heart failure patients may have fluid accumulation in the lungs that may cause an elevation of ventricular filling pressure. Worsening heart failure may be accompanied by diastolic dysfunction, resulting pathologically louder S3, Profound S4 may also be present in HF patients due to forceful atrial contraction to overcome an abnormally stiff ventricle. Therefore, S3 or S4 heart sounds may be detected to qualify diastolic dysfunction and to generate diagnostics of WHF. However, because S3 and S4 generally have relatively weaker signal intensity and lower frequency than other HS components such as S1 or S2, detection of S3 and S4 can be challenging. The HS signal may be susceptible to interferences such as due to physical activity or motions. Detection of heart sound components may also be challenging at higher heart rate or during cardiac electrostimulation. The present inventors have recognized there remains a need for systems and methods to more reliably and accurately detect HS components such as S3 or S4 for diastolic dysfunction assessment and WHF detection.

This document discusses, among other things, a patient management system for monitoring and treating patients with heart failure. The system may include a signal receiver to receive a heart sound (HS) signal and an impedance signal sensed from the patient, such as via one or more physiological sensors. A heart sound detector circuit may use at least the received impedance signal to determine a HS detection window, and detect a HS component indicative of cardiac diastolic function from the received HS signal within the HS detection window. The system may include a heart failure detector circuit to generate a cardiac diastolic function indicator (DFI) using the detected HS component and, in certain examples, may detect worsening heart failure (WHF) based on the generated DFI. The system may include an optional therapy circuit to deliver or adjust an electrostimulation therapy based on the determined DFI.

Example 1 is a system for managing heart failure in a patient. The system comprises: a signal receiver circuit configured to receive a heart sound (HS) signal and an impedance signal sensed from the patient, a heart sound detector circuit configured to: determine a HS detection window corresponding to a cardiac diastolic period using the received impedance signal; and detect at least one EIS component from the received HS signal within the determined HS detection window, the at least one EIS component indicative of cardiac diastolic function; and a heart failure detector circuit configured to generate a cardiac diastolic function indicator (DFI) using the detected at least one HS component.

In Example 2, the subject matter of Example 1 optionally includes the at least one HS component indicative of cardiac diastolic function that may include a third heart sound (S3) and a fourth heart sound (S4). The heart sound detector circuit may be configured to determine an S3 detection window and an S4 detection window using the received impedance signal, and detect S3 from the received HS signal within the S3 detection window and detect S4 from the received HS signal within the S4 detection window.

In Example 3, the subject matter of Example 2 optionally includes the heart failure detector circuit that may be configured to generate the DFI using a ratio of an intensity of the detected S3 to an intensity of the detected S4.

In Example 4, the subject matter of any one or more of Examples 1-3 optionally includes the heart failure detector circuit that may be configured to detect worsening heart failure using the generated DFI, and a therapy circuit configured to deliver or adjust a therapy when the generated DFI satisfies a specified condition.

In Example 5, the subject matter of Example 4 optionally includes the therapy that may include cardiac electrostimulation. The therapy circuit may be configured to adjust a stimulation timing parameter using the DFI, and deliver the cardiac electrostimulation according to the determined stimulation timing parameter.

In Example 6, the subject matter of Example 5 optionally includes the stimulation timing parameter that may include an atrio-ventricular delay (AVD) or interventricular delay (VVD) with respect to a reference event for initiating a ventricular pacing therapy. The therapy circuit may be configured to determine the stimulation timing parameter, which may include measuring the DFI in response to the ventricular pacing delivered according to the stimulation timing parameter programmed at a plurality of candidate values and selecting from the plurality of candidate values a stimulation timing parameter value when the corresponding measured DFI satisfies a specific condition.

In Example 7, the subject matter of any one or more of Examples 1-6 optionally includes the heart sound detector circuit that may be configured to detect an impedance portion of the received impedance signal that temporally corresponds to a passive ventricular filling period or an active ventricular filling period, and determine the HS detection window using the detected impedance portion.

In Example 8, the subject matter of Example 7 optionally includes the heart sound detector circuit that may be configured to determine, from the received HS signal, an initial HS detection window based on a heart rate, and determine the HS detection window using the initial HS detection window and the detected impedance portion.

In Example 9, the subject matter of Example 8 optionally includes the heart sound detector circuit that may be configured to detect a second heart sound (S2) timing using a linear function of heart rate, determine the initial HS detection window that begins at a specific delay from the detected S2 timing, and adjust the linear function using the detected impedance portion.

In Example 10, the subject matter of Example 9 optionally includes the heart sound detector circuit that may be configured to adjust the linear function including a slope or an intercept of eth linear function.

In Example 11, the subject matter of any one or more of Examples 9-10 optionally includes the heart sound detector circuit that may be configured to adjust the linear function periodically or in response to a trigger event.

In Example 12, the subject matter of any one or more of Examples 8-11 optionally includes the heart sound detector circuit that may be configured to determine a signal quality measure of the received HS signal and a signal quality measure of the received impedance signal, and select between the initial HS detection window and the detected impedance portion to determine the HS detection window using a comparison between the signal quality measure of the received HS signal and the signal quality measure of the received impedance signal.

In Example 13, the subject matter of Example 12 optionally includes the heart sound detector circuit that may be configured to determine the signal quality measure of the received impedance signal using a signal strength of the detected impedance portion temporally corresponding to a passive ventricular filling period or an active ventricular filling period.

In Example 14, the subject matter of any one or more of Examples 12-13 optionally includes the heart sound detector circuit that may be configured to determine the signal quality measure of the received impedance signal using a sensitivity of the detected impedance portion to a change in ventricular diastolic function.

In Example 15, the subject matter of Example 14 optionally includes the heart sound detector circuit that may be configured to determine sensitivity of the detected impedance portion based on a comparison of the impedance portion detected during cardiac electrostimulation according to at least two different stimulation configurations.

Example 16 is a system for managing heart failure in a patient. The system comprises: a signal receiver configured to receive a heart sound (HS) signal and an impedance signal sensed from the patient; a heart sound detector circuit configured to: detect, from the received impedance signal, a first impedance portion temporally corresponding to a passive ventricular filling period, and a second impedance portion temporally corresponding to an active ventricular filling period; determine a third heart sound (S3) detection window using the first impedance portion and a fourth heart sound (S4) detection window using the second impedance portion; and detect S3 from the received HS signal within the S3 detection window, and detect S4 from the received HS signal within the S4 detection window; a heart failure detector circuit configured to generate a cardiac diastolic function indicator (DFI) using a ratio of an intensity of the detected S3 to an intensity of the detected S4; and a therapy circuit configured to determine a stimulation timing parameter using the DFI, and deliver cardiac electrostimulation according to the determined stimulation timing parameter.

In Example 17, the subject matter of Example 16 optionally includes the heart sound detector circuit that may be configured to: detect, from the received HS signal, a second heart sound (S2) timing using a linear function of heart rate; adjust a parameter of the linear function using information extracted from the first or second impedance portion; and determine at least one of the S3 detection window or the S4 detection window based on a S2 timing estimated using the linear function with the adjusted parameter.

Example 18 is a method for managing heart failure in a patient using a medical system. The method comprises steps of: receiving a heart sound (HS) signal and an impedance signal sensed from the patient; determining, via a heart sound detector circuit, a HS detection window corresponding to a cardiac diastolic period from the received impedance signal; detecting, via the heart sound detector circuit, at least one HS component from the received HS signal within the determined HS detection window, the at least one HS component indicative of cardiac diastolic function; generate a cardiac diastolic function indicator (DFI) using the detected at least one HS component; and detecting worsening heart failure using the DFI using a heart failure detector circuit.

In Example 19, the subject matter of Example 18 optionally includes steps of: determining the HS detection window includes determining, from the received impedance signal, an S3 detection window and an S4 detection window; detecting the at least one HS component includes detecting S3 from the received HS signal within the S3 detection window and detecting S4 from the received HS signal within the S4 detection window; and generating the DFI using a ratio of an intensity of the detected S3 to an intensity of the detected S4.

In Example 20, the subject matter of Example 18 optionally includes, comprising delivering or adjusting a therapy when the determined DFI satisfies a specific condition.

In Example 21, the subject matter of Example 18 optionally includes determining the HS detection window from the received impedance signal that may include: detecting, from the received impedance signal, an impedance portion temporally corresponding to a passive ventricular filling period or an active ventricular filling period; and determining the HS detection window using the detected impedance portion In Example 22, the subject matter of Example 21 optionally includes determining the HS detection window from the received impedance signal, which may include: determining from the received HS signal an initial HS detection window as a function of heart rate; adjusting a parameter of the function using information extracted from the detected impedance portion; and determining the HS detection window using the function with the adjusted parameter.

In Example 23, the subject matter of Example 31 optionally includes determining the HS detection window from the received impedance signal, which may include: determining a signal quality measure of the received HS signal and a signal quality measure of the received impedance signal; and selecting between the initial HS detection window and the detected impedance portion to determine the HS detection window based on the signal quality measure of the received HS signal and the signal quality measure of the received impedance signal.

In Example 24, the subject matter of Example 23 optionally includes the signal quality measure of the received impedance signal that may include at least one of: a signal strength of the detected impedance portion temporally corresponding to a passive ventricular filling period or an active ventricular filling period; or a sensitivity of the detected impedance portion to cardiac electrostimulation according to at least two different stimulation configuration.

The systems, devices, and methods discussed in this document may improve the medical technology of device-based heart failure patient management. Assessment of diastolic dysfunction using heart sounds components corresponding to passive and active ventricular filling, such as S3 and S4, may enhance the performance and functionality of a medical system or an ambulatory medical device for detecting WHF. Compared to conventional methods where the HS components are detected from the detection windows that are determined solely based on the heart sound signal, the present document discusses S3 and S4 detection windows that are determined using a reference signal such as a thoracic impedance signal. This is advantageous because more reliable estimate of S3 and S4 locations may be achieved when heart sound signal has a poor signal quality such as due to interference from patient physical activities, or when the reference signal such as a thoracic impedance is more sensitive to changes to ventricular diastolic phases and immune to noise. As such, with improve quantitative assessment of diastolic function, the systems and methods discussed herein may timely and reliably detect events leading to WHF at little to no additional cost. Such improvement in system performance and functionality can reduce healthcare costs associated with HF management and hospitalization. Additionally, the systems, devices, and methods discussed in this document may also allow for more efficient device memory usage, such as by storing the diastolic function indicators (DFI) that are clinically more relevant to diagnosis of WHF. As fewer false positive detections of WHF events are provided, device battery life can be extended, fewer unnecessary drugs and procedures may be scheduled, prescribed, or provided. Therapy titration, such as electrostimulation parameter adjustment, based on DFI may not only improve therapy efficacy and patient outcome, but may also save device power. As such, overall system cost savings may be realized.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring patients with cardiac diseases such as heart failure. The system may include a signal receiver configured to receive a heart sound (HS) signal and an impedance signal sensed from the patient. A heart sound detector circuit may be configured to determine a HS detection window using at least the received impedance signal. The HS detection window may be used to detect HS components indicative of cardiac diastolic function. The heart sound detector may detect the HS components from the received HS signal within the determined HS detection window. A heart failure detector circuit may generate a cardiac diastolic function indicator (DFI) based on the detected HS components. A therapy circuit may deliver or adjust an electrostimulation therapy based on the determined DFI.

Figure 1:
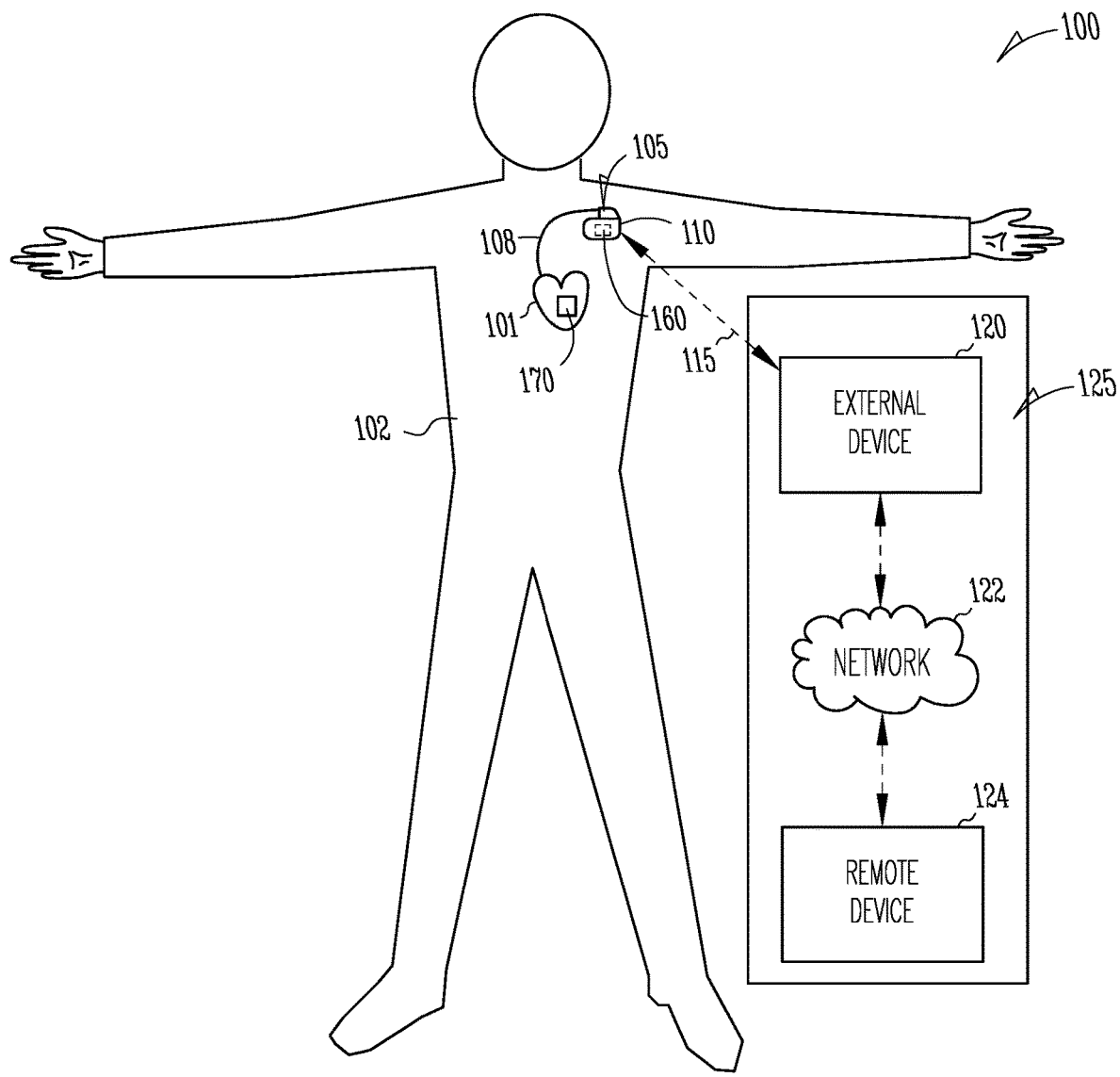
FIG. 1 illustrates generally an example of a patient management system and portions of an environment in which the system may operate.

FIG. 1 illustrates generally an example of a patient management system 100 and portions of an environment in which the system 100 may operate. The patient management system 100 may include an ambulatory system 105 associated with a patient 102, an external system 125, and a telemetry link 115 providing for communication between the ambulatory system 105 and the external system 125. In certain examples, the patient management system 100 may be configured as a heart failure management system to perform a range of acts including, for example, monitoring patient heart failure status, generating an alert of patient worsening heart failure (WHF), delivering a therapy or adjusting an existing therapy to treat heart failure or to alleviate heart failure comorbidities, or providing feedback on therapy efficacy, such as patient physiological responses to a therapy, to a system user such as a clinician.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, or external monitoring or therapeutic medical devices such as automatic external defibrillators (AEDs) or Holter monitors; wearable medical devices such as patch-based devices, smart watches, or smart accessories; or a bedside monitor.

By way of example, the AMD 110 may be coupled to the lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The lead system 108 and the associated electrodes may deliver therapy to treat cardiac or pulmonary diseases. The therapies may include pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. In an example, the lead system 108 and the associated electrodes may be implanted subcutaneously or wearable on the patient body. The associated electrodes on the lead system 108 may be positioned at the patient's thorax or abdomen to sense intrinsic physiological signals indicative of cardiac or pulmonary activities, or physiological responses to diagnostic or therapeutic stimulations to a target tissue. In certain examples, the ambulatory system 105 may include one or more leadless sensors not being tethered to the AMD 110 via the lead system 108. The leadless ambulatory sensors may be configured to sense a physiological signal and wirelessly communicate with the AMD 110.

The AMID 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, heart rate, heart rate variability, thoracic impedance, cardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature, among others. In some examples, the AMD 110 may be coupled to a data storage device, such as an electronic medical record (EMR) system, and receive physiological data from the data storage device.

The patient management system 100 may include a monitor circuit 160 for monitoring patient health status. The monitor circuit 160 may be substantially enclosed within the AMD 110 as illustrated in FIG. 1, or alternatively may be substantially included in the external system 125, or distributed between the ambulatory system 105 and the external system 125. The monitor circuit 160 may be configured to monitor patient heart failure status, such as to detect an event leading to worsening heart failure (WEIR The monitor circuit 160 may analyze the physiological data, such as acquired by the ambulatory system 105 or received from a data storage device, for patient monitoring, risk stratification, and detection of events indicating presence, onset, termination, improvement, or worsening of a disease or health condition, such as heart failure. In certain examples, the monitor circuit 160 may include sub-circuits to detect one or more heart sound components such as S1, S2, S3, or S4 from a heart sound signal. The heart sound components, such as S3 or S4, may be detected within their respective detection windows that are determined using one or more physiological signals, such as a thoracic impedance signal. As previously discussed, S3 and S4 are indicative of patient cardiac diastolic function. The monitor circuit 160 may generate an indicator of cardiac diastolic function (DFI) using S3, S4, or a combination of S3 and S4. In some examples, the monitor circuit 160 may generate DFI from a portion of the thoracic impedance signal. Examples of the monitor circuit 160 are discussed below, such as with reference to FIGS. 4-5.

The AMD 110 may additionally include a therapy circuit configured to initiate or adjust therapies for treating a condition such as WHF. The therapy may be delivered to the patient 102, via the lead system 108 and the associated electrodes. The therapies may include electrical, magnetic, or other types of energy. Examples of the therapies may include cardiac pacing, cardioversion, defibrillation, neuromodulation, among other electrostimulation therapies. In an example, the therapy circuit may deliver cardiac resynchronization therapy (CRT) or multi-site pacing at least one ventricle to rectify dyssynchrony and to improve cardiac function in a CHF patient. The therapy may be initiated, or one or more therapy parameters may be adjusted, based on DFI. In some examples, the AMD 110 may deliver drug therapies or biological therapies, such as via a drug infusion pump or other drug delivery systems.

In certain examples, the ambulatory system 105 may include a leadless medical device (LMD) 170. The LMD 170 may include a device body, and one or more electrodes positioned on an outer surface of the device body. Unlike a tethered device (such as the AMD 110 coupled to the lead system 108), the LMD 170 requires no lead, wire, or tether extended between the electrodes and the device body. The LMD 170 may include an anchoring or fixation mechanism for positioning the LMD 170 on a target implant side, such as an endocardial surface of one of a left ventricle, a right ventricle, a left atrium, or a right atrium, or an epicardial surface of a portion of the heart. The LMD 170 may be delivered transvenously and positioned within a blood vessel on the heart, such as a coronary vein, where one or more electrodes on the LMD 170 may be directly or indirectly in contact with the epicardial surface of the heart. An example of such an LMD 170 may include the leadless cardiac pacemaker (LCP) disclosed in the commonly assigned U.S. Patent Application Publication US2016/0051823 by Maile et al., entitled "LEADLESS CARDIAC PACEMAKER HAVING A SENSOR WITH A LOWER POWER MODE," which is hereby incorporated by reference in its entirety.

The LMD 170 may house circuitry that couples to the one or more electrodes to sense cardiac electrical activity. The LMD 170 may additionally include one or more physiological sensors configured to acquire physiological data including, for example, a blood pressure signal, a heart sound signal, a blood-oxygen saturation measurement, a temperature measurement, a blood flow signal, or a blood chemical measurement, among others. In an example, the LMD 170 may include an accelerometer sensor configured to sense an epicardial or endocardial acceleration (EA) signal from a portion of a heart. The EA signal, or the peak endocardial acceleration (PEA) signal, may be indicative of force generated while the heart (or a portion such as right or left ventricle) contracts or relaxes. The EA signal may be correlated to one or more heart sound components, such as the S1, S2, S3 or S4 heart sounds, and may be used to assess cardiac systolic or diastolic function.

The LMD 170 may include circuitry that enables communication with the AMD 110. Through an established communication link, the LMD 170 may perform various functionalities including, for example, receive a sense command from the AMD 110 for sensing the EA signal, or transmit the sensed EA signal to the AMD 110. The monitor circuit 160, such may detect heart sounds components, such as S3 or S4, from the EA signal provided by the LMD 170 within respective heart sound detection windows, and generate a heart failure diagnostic indicating patient cardiac diastolic function.

The LMD 170 may include a therapy circuit that can deliver a therapy to the patient, such as electrostimulation of a target cardiac tissue, neural tissue, or other tissues that the electrodes of the LIVID are in contact with or have an effect on. In an example, the LMD 170 may deliver cardiac pacing therapy from a region inside a heart chamber or on the epicardial surface of the heart.

The external system 125 may include a dedicated hardware/software system such as a programmer, a remote server-based patient management system, or alternatively a system defined predominantly by software running on a standard personal computer. Via a communication link 115, the external system 125 may program the AMD 110 to perform one or more of acquiring physiological data, performing at least one self-diagnostic test (such as for a device operational status), analyzing the physiological data to detect a cardiac event such as WHF, or optionally delivering or adjusting a therapy to the patient 102. Additionally, the external system 125 may receive device data from the AMD 110 via the communication link 115. Examples of the device data received by the external system 125 may include real-time or stored physiological data from the patient 102, diagnostic data such as detection of WHF events, responses to therapies delivered to the patient 102, or device operational status of the AMD 110 (e.g., battery status and lead impedance). In some examples, the external system 125 may be configured to control the LMD 170, such as cardiac activity sensing or therapy delivery via the one or more electrodes, or sensing a physiological signal via a physiological sensor included in the LMD 170. The patient management system 100 may optionally include another external system (not shown) separate from the external system 125, which is dedicated for programming the DAD 170. The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards, among other configurations and combinations of data source interfacing.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The remote device 124 may evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. In some examples, the alert conditions may alternatively or additionally be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning, such as respectively described in commonly-assigned U.S. patent application, entitled, "System and Method for Managing Coordination of Assembled Patient Data in an Automated Patient Management System," Ser. No. 11/121,593, filed May 3, 2005, and patent application, entitled, "System and Method for Managing Patient Triage in an Automated Patient Management System," Ser. No. 11/121,594, filed May 3, 2005, the disclosures of which are incorporated by reference. In addition to generating alert notifications, the remote device 124, including the server and the interconnected clients, may also execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a system user such as the patient or a clinician, or to a process including, for example, an instance of a computer program executable in a microprocessor. In an example, the process may include an automated generation of recommendations for therapy; adjustment of one or more therapy control parameters such as electrostimulation timing or sequence, electrostimulation mode or amount of stimulation energy, electrode configurations, or stimulation site selection; or a recommendation for further diagnostic test. In an example, the external device 120 or the remote device 124 may include a respective display unit for displaying the physiological or functional signals, or alerts, alarms, emergency calls, or other forms of warnings to signal. In some examples, the external system 125 may include an external data processor configured to analyze the physiological or functional signals received by the AMD 110, and to confirm or reject the detection of the cardiac events such as WHF. Computationally intensive algorithms, such as machine-learning algorithms, may be implemented in the external data processor to process the data retrospectively to detect the cardiac events.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
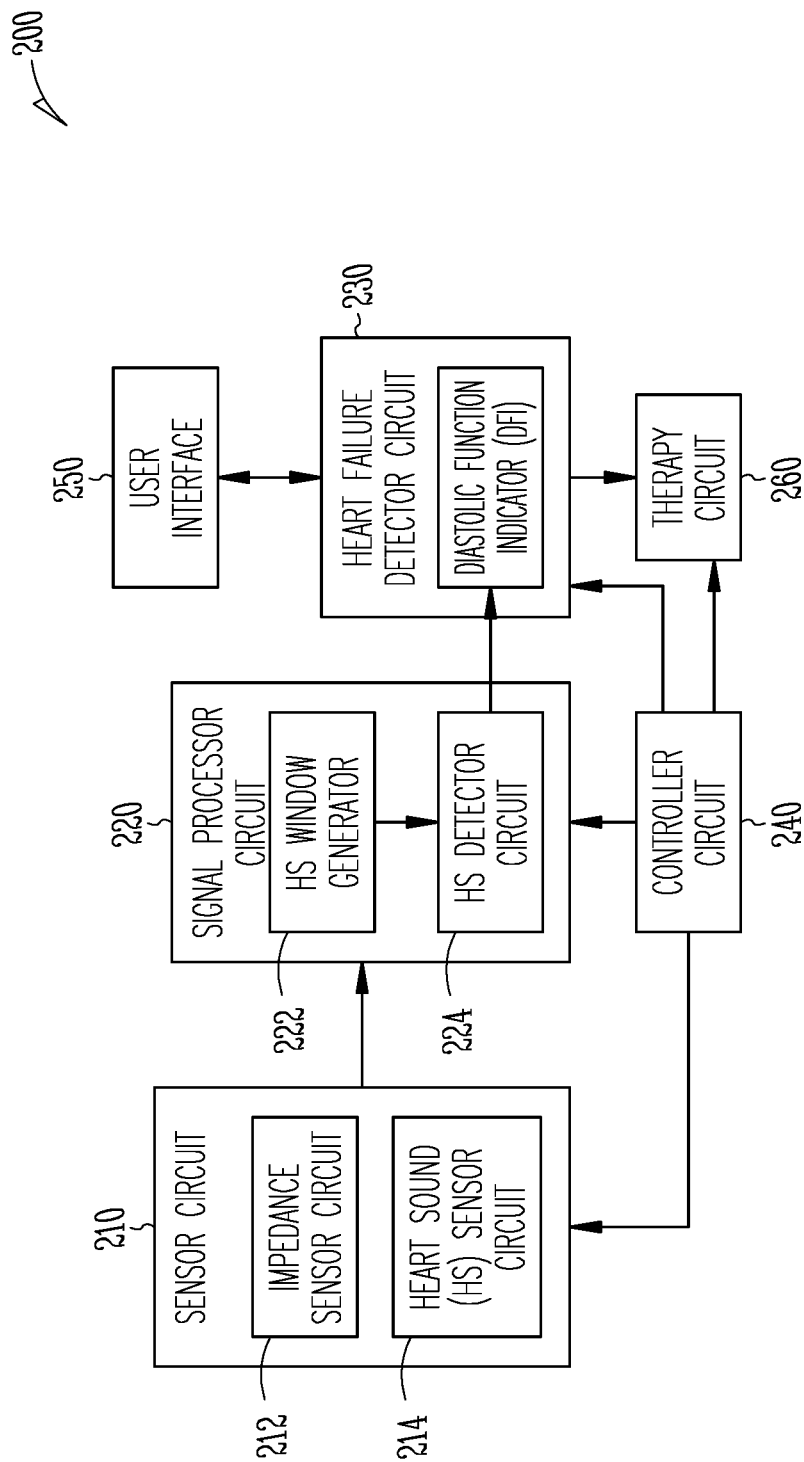
FIG. 2 illustrates generally an example of a cardiac monitoring system for monitoring cardiac function, such as a progression of a heart failure or other cardiac disease.

FIG. 2 illustrates generally an example of a cardiac monitoring system 200 for monitoring cardiac function, such as a progression of a heart failure or other cardiac disease. The cardiac monitoring system 200 may provide diagnostic decisions, recommend treatment, deliver or adjust therapies based on the cardiac monitoring. The cardiac monitoring system 200 may include one or more of a sensor circuit 210, a signal processor circuit 220, a heart failure detector circuit 230, a controller circuit 240, and a user interface 250. In some examples, the cardiac monitoring system 200 may additionally include a therapy circuit 260 configured to deliver or adjust a therapy to treat or to prevent WHF. At least a portion of the cardiac monitoring system 200 may be implemented within the AMD 110, distributed between two or more implantable or wearable medical devices or between the AMD 110 and the external system 125.

The sensor circuit 210 may include an impedance sensor circuit 212 and a heart sound sensor circuit 214. The impedance sensor circuit 212 may be coupled to impedance sensors, such as electrodes located on one or more leads of the lead system 108 or the housing of the AMD 110 (hereinafter referred to as "can electrode"). The impedance sensor circuit 212 may inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing. For example, the impedance may be sensed between an electrode disposed in the right atrium (RA) and the can electrode ($Z_{RA-Can}$), between an electrode disposed in the right ventricle (RV) and the can electrode ($Z_{RV-Can}$), or between an electrode disposed at an epicardia surface of left ventricle (LV) such as inside a cardiac vein and the can electrode ($Z_{LV-Can}$). The impedance may include an impedance vector where the voltage sensing electrodes and the current injection electrodes are substantially orthogonal to each other. For example, the current may be injected between an RA electrode and an RV electrode, and the resulting voltage is sensed between an RN electrode and an LV electrode ($Z_{RA-RV-LV}$). The impedance sensor circuit 212 may preprocess the sensed signal, including amplification, digitization, filtering, or other signal conditioning operations.

The HS sensor circuit 214 may be coupled to a heart sound sensor to sense a heart sound signal including one or more of HS components such S1, S2, S3 or S4. The heart sound sensor may take the form of an accelerometer, an acoustic sensor, a microphone, a piezo-based sensor, or other vibrational or acoustic sensors. The HS sensor may be included in the AMD 110, or disposed on a lead such as a part of the lead system 108. In some examples, the HS sensor circuit 214 may be communicatively coupled to an accelerometer sensor associated with the LMD 170. The accelerometer sensor can be a two-axis or a three-axis accelerometer sensor. Examples of the accelerometer may include flexible piezoelectric crystal (e.g., quartz) accelerometer or capacitive accelerometer, fabricated using micro electro-mechanical systems (MEMS) technology. The accelerometer sensor may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to the S1, S2, S3, and S4 heart sounds, respectively. For example, like the S3 and S4 heart sounds, the EA signal may include a component representing vibrational forces of the ventricular walls during rapid and passive ventricular filling, and another component representing atrial contraction and active ventricular filling during the diastole. In this document, the EA signal such as sensed from the DAD 170 and the HS signal sensed from an ambulatory sensor are collectively referred to as the "HS signal." The HS components, such as S1, S2, S3, or S4, also include components extracted from the EA signal, such as signal portions corresponding to the respective HS components in a HS signal sensed by a HS sensor.

The HS sensor circuit 214 may pre-process the sensed HS signal, including amplification, digitization, filtering, or other signal conditioning operations. In an example, the HS sensor circuit 214 may include a bandpass filter adapted to filter the sensed HS signal to a frequency range of approximately between 5 and 90 Hz, or approximately between 9 and 90 Hz. In an example, the physiological sensor circuit 222 may include a double or higher-order differentiator configured to calculate a double or higher-order differentiation of the sensed HS signal.

The signal processor circuit 220 may be coupled to the sensor circuit 210 to receive the impedance signal and the HS signal. In some examples, the system 200 may include a receiver circuit coupled to a data storage device, such as an electronic medical record (EMR) system, for storing HS signals and impedance signals sensed from a patient, optionally along with other physiologically signals such as ventricular pressure signals or cardiac wall tension or strain signals. The signal processor circuit 220 may retrieve an impedance signal and a HS signal from the storage device. The impedance signal and the HS signals may be simultaneously sensed from the same patient, and are time-synchronized. In an example, the signal processor circuit 220 may include a calibration circuit to time-synchronize the impedance signal with the HS signals to remove or substantially reduce the data acquisition system delay and/or physiological delay between the impedance signal and the HS signal. For example, the time synchronization may be achieved by aligning the impedance signal with the HS signals using synchronization markers generated before or during data acquisition.

The signal processor circuit 220 and the heart failure (HF) detector circuit 230 may be configured to detect heart sounds and generate a diastolic function indicator (DFI) using the detected heart sounds. The signal processor circuit 220 and the FIT detector 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The signal processor circuit 220 and the HF detector 230 may each include circuit sets comprising one or more other circuits or sub-circuits. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the signal processor circuit 220 may include a HS window generator 222 and a HS detector circuit 224. The HS window generator 222 may determine a HS detection window for detecting a HS component, such as one or more of an S3 detection window $W_{S3}$ or an S4 detection window $W_{S4}$ within the same cardiac cycle. Each HS detection window W is defined by a start time ($T_1$) and an end time ($T_2$). The HS detections windows, such as $W_{S3}$ and $W_{S4}$, may be determined using at least the impedance signal. The impedance may change as a result of changes in tissue characteristics in the electrode vector field such as disease-induced tissue degradation, or a change in distance between impedance sensing electrodes, and/or a change in blood volume contained with the electrode vector field. During a cardiac cycle, the cardiac systole and diastole may be accompanied by changes in electrode spacing, cardiac tissue properties, and blood volume. As to be discussed with reference to FIG. 3, the impedance measurement during a cardiac cycle may provide temporal information about the passive ventricular filling period (during which S3 may occur) and subsequent atrial contraction and active ventricular filling period (during which S4 may occur). In another example, the HS window generator 222 may determine one or more of $W_{S3}$ or $W_{S4}$ using the impedance signal and at least another physiological signal, such as a HS signal. In yet another example, the HS window generator 222 may select from a plurality of physiological signals, such as between the impedance signal and the HS signal, a signal for use to determine one or more of $W_{S3}$ or $W_{S4}$. Examples of the HS window determination are discussed below, such as with reference to FIGS. 4A-D.

Although the discussion of HS window generation with reference to FIG. 2 and throughout this document focuses on the thoracic impedance, this is meant only by way of example and not limitation. Other physiological signals, such as ventricular pressure signal, ventricular wall stress, strain, or tension or force signal may additionally or alternatively be used as reference signals to determine HS windows such as S3 window or S4 window, and to guide HS detection and diastolic function assessment. The pressure or stress sensors may be positioned at or near an endocardial or epicardial location of the ventricles. In an example, the sensors may be incorporated into the LMD 170.

The HS detector circuit 224 may detect at least one HS component from the received HS signal within the determined HS detection window. In an example, the HS detector circuit 224 may detect S3 sound from the received HS signal within the S3 detection window, and detect S4 sound from the received HS signal within the S4 detection window. The detection can be based on signal amplitude, signal energy, or other intensity measure of the portion of the HS signal within the respective HS detection window. For example, an S3 is detected when the signal amplitude, signal energy, or other signal intensity measures within the S3 detection window exceeds a specific threshold. Similarly, an S4 is detected when the signal amplitude, signal energy, or other signal intensity measures within the S4 detection window exceeds a specific threshold, in some examples, the HS detector circuit 224 may detect an HS component such as S3 or S4 adaptively by tracking the temporal locations of the previously detected HS features. For example, an S3 heart sound may be detected by adaptively tracking the timing of historically detected S3 heart sounds. A dynamic programming algorithm may be used to detect and track the S3 heart sound within the S3 detection window, such as that disclosed in the commonly assigned Patangay et al. U.S. Pat. No. 7,853,327 entitled "HEART SOUND TRACKING SYSTEM AND METHOD," which is hereby incorporated by reference in its entirety.

The heart failure detector circuit 230 may generate a cardiac diastolic function indicator (DFI) using the detected at least one HS component, such as measurements taken from the detected S3 or S4, or a combination of measurements taken from S3 and S4. DFI may be represented as a numerical value or a categorical value, and indicate patient cardiac diagnostic function, such as reduced ventricular wall compliance or restrictive ventricular filling. The heart failure detector circuit 230 may detect WHF when DFI satisfies a specific condition, such as when DFI exceeds a threshold value or falls within a specified value range.

In an example, DFI may be determined using S3 intensity, denoted by $\|S3\|$. The S3 intensity may be computed using S3 amplitude or signal energy within the S3 detection window. In another example, DPI may be determined using S4 intensity, denoted by $\|S4\|$. A louder S3 such as the $\|S3\|$ exceeding an S3 intensity threshold, or a profound S4 intensity such as the $\|S4\|$ exceeding an S4 intensity threshold, may indicate reduced compliance of the ventricles and deterioration of diastolic function, and can be used to detecting WHF.

In various examples, DPI may be computed using a combination of $\|S3\|$ and $\|S4\|$. The combination can be linear or nonlinear. In an example, DFI may be computed using the HS intensity ratio $\|S3\|/\|S4\|$. S3 and S4 may respectively correspond to the E wave and A wave as seen in a Doppler echocardiograph, and the HS intensity ratio $\|S3\|/\|S4\|$ may be related to E wave to A wave ratio (E/A) derived from the echocardiograph. The E wave and A wave are two peaks on the transmitral flow profile. The E wave arises due to early passive diastolic filling, which accounts for 70-75% of the ventricular filling during this phase. The A wave arises due to atrial contraction, forcing approximately 20-25% of stroke volume into the ventricle.

Morphological parameters from the E wave and A wave from echocardiograph have been used to assess ventricular diastolic function. Among others, two such parameters are E wave intensity to A wave intensity ration (E/A) and the E wave deceleration time (DT). The E/A ratio represents a relative velocity of blood flow during the early and late phases of diastole. The DT is the time taken from the maximum E point to baseline. In a subject with normal diastolic function, the E velocity is greater than the A velocity, and E/A ratio is normally within a range of approximately between 1 and 1.5. The DT may generally fall within a range of approximately 160-220 milliseconds (msec). In certain pathologies and with aging, the left ventricular wall can become stiff, increasing the back pressure as it fills. This may slow the early (E) filling velocity, thus lowering the E/A ratio. In heart failure patients with impaired relaxation (a relatively mild diastolic dysfunction), the left ventricular wall can become so stiff as to impair proper filling. The E wave may become reduced, representing a transmitral velocity that may be even slower than the subsequent A wave velocity. Correspondingly, the E/A ratio may be less than 1. Along with the reduced E/A ratio, which is often accepted as a clinical marker of diastolic dysfunction, the E wave may be broader, and the DT can be greater than 22.0 msec. In patients with restrictive diastolic function (a relatively severe dysfunction), however, E wave velocity may increase more than an increase in A wave velocity, resulting in a E/A ratio greater than 1.5 or even greater than 2. The E wave is also represented as a sharper peak. The DT can fall below a threshold value of approximately 150 msec.

S3 and E wave both occur during the early passive filling period, and respectively represent cardiac vibration and blood flow velocity caused by the early passive filling of blood into the ventricles. S4 and A wave both occur during the subsequent active filling period, and respectively represent cardiac vibration and blood flow velocity caused by subsequent atrial contraction that actively pushes the blood into the ventricles. HS intensity ratio $\|S3\|/\|S4\|$ may be used to estimate the E/A ratio. The heart failure detector circuit 230 may generate DFI using a comparison of the HS intensity ratio $\|S3\|/\|S4\|$ to a healthy value range defined by a lower threshold value and a higher threshold value. If $\|S3\|/\|S4\|$ falls within the healthy value range, DFI indicates no substantial diastolic dysfunction. If $\|S3\|/\|S4\|$ exceeds the upper threshold value, restrictive ventricular filling is indicated. If $\|S3\|/\|S4\|$ falls below the lower threshold value, impaired diastolic function is indicated.

The S3 amplitude is found be inversely correlated to DT in some HF patients. A stronger $\|S3\|$ may correspond to a shorter DT, indicating more restrictive ventricular filling and worsening of diastolic function. In an example, DFI may be determined using S3 as an estimate of DT. Using the inverse relationship between DT and the S3 amplitude, an upper threshold bound ($\|S3\|_{TH1}$) corresponding to the lower DT threshold of approximately 150-160 msec, and a lower threshold bound ($\|S3\|_{TH2}$) corresponding to the upper DT threshold of approximately 220 msec, may be determined. A $\|S3\|$ that is greater than $\|S3\|_{TH1}$ may correspond to DT of less than 150 or 160 msec, indicating severe diastolic dysfunction with restrictive filling pattern. A $\|S3\|$ that is less than $\|S3\|_{TH2}$ may correspond to DT greater than 220 msec, indicating mild diastolic dysfunction with impaired relaxation. In some examples, DFI may be a composite index computed using both the intensity ratio $\|S3\|/\|S4\|$ and $\|S3\|$. The DFI thus determined provides an estimate of cardiac diastolic function based on the E/A ratio and the DT.

In addition to or in lieu of S3 or S4 intensity or a combination thereof, DFI may alternatively be computed using other HS signal metrics generated from the detected S3 or S4 heart sounds, or from the signal portions within the S3 detection window or the S4 detection window. In an example, DFI may be determined using a slope of S3 peak within the S3 detection window, or a slope of S4 peak within the S4 detection window. In another example, DFI may be determined using a frequency of the HS signal portion within the S3 detection window, or a frequency of the signal portion within the S4 detection window. In various examples, DFI may be computed using a linear or nonlinear combination of one or more S3 metrics and/or S4 metrics.

The control circuit 240 may control the operations of the sensor circuit 210, the signal processor circuit 220, the heart failure detector circuit 230, and the data and instruction flow between these system components. The user interface 250 may include an output unit to generate a human-perceptible presentation of diagnostic information, such as a display of DFI, optionally along with other information such as one or more of the sensed impedance signal, the sensed HS signal, the detected HS components such as S3 and S4, or diagnostic information about the detection of WHF. The output unit 230 may include a display for displaying the information, or a printing device for producing a hardcopy of the information. The information may be presented in a table, a chart, a diagram, or any other types of textual, tabular, or graphical presentation formats. The presentation of the output information may include audio or other media format to alert the system user of the detected WHF event. The user interface 250 may also include input device such as a keyboard, on-screen keyboard, mouse, trackball, touchpad, touch-screen, or other pointing or navigating devices. The input device may enable a system user such as a clinician to program the parameters used for sensing the impedance or HS signals, defining the HS detection windows, and detecting one or more HS components. In an example, at least a portion of the user interface 250 may be implemented in the external system 125.

The system 200 may optionally include a therapy circuit 260 that may generate and deliver a therapy to the patient. The therapy may be triggered in response to DFI satisfying a specified condition, such as exceeding a specific threshold or falling within a specific range indicating WHF. The therapy may be delivered in response to a user command such as received via the user interface 250. Examples of the therapy may include electrostimulation therapy delivered a cardiac tissue, a nerve tissue, or other target tissues, or drug therapy including delivering drug to a tissue or organ. The electrostimulation may be delivered to a region inside a heart chamber or on the epicardial surface of the heart. In an example, the therapy circuit 260 may deliver electrostimulation including cardiac resynchronization therapy (CRT), or multi-site pacing at a heart chamber such as a left ventricle. The control circuit 250 may control the therapy circuit 260 by adjusting one or more therapy control parameters when DFI satisfies a specific condition. Examples of therapy control using DFI are discussed below, such as with reference to FIG. 5.

Figure 3:
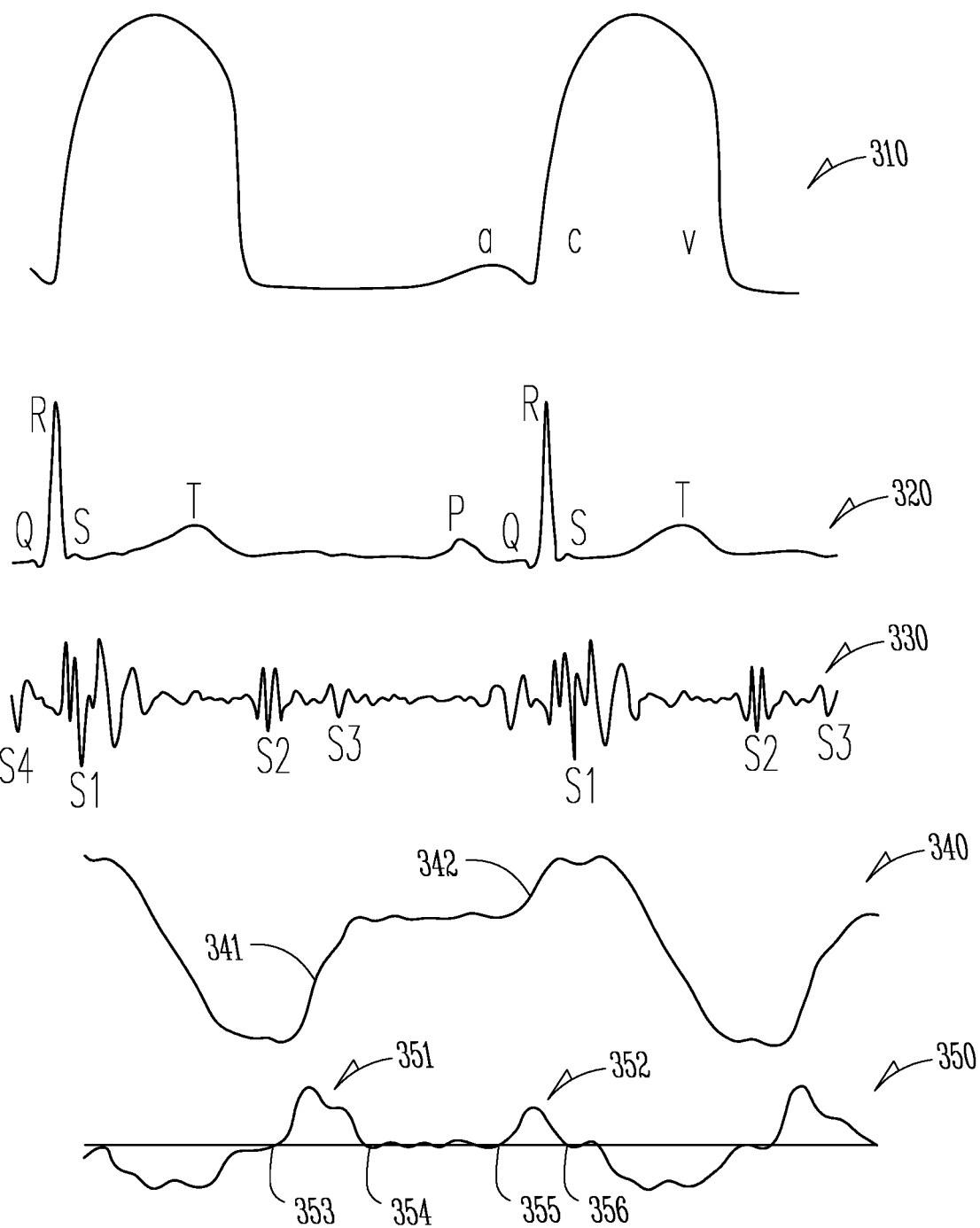
FIG. 3 illustrates generally an example of graphical depiction of physiological signals during consecutive cardiac cycles.

FIG. 3 illustrates generally an example of graphical depiction of physiological signals during consecutive cardiac cycles, including a left ventricular pressure (LVP) signal 310, an electrocardiograph (ECG) signal 320, a heart sound (HS) signal 330, a conductance signal 340, and a conductance derivative signal 350. The signals may be simultaneously recorded, or time-synchronized to remove or substantially reduce the data acquisition system delay and/or physiological delay between one physiological signal and another physiological signal. The resulting signals, as illustrated in FIG. 3, reveal temporal relationship among various signal portions at different phases of a cardiac cycle.

The physiological signals may be sensed using physiological sensors. By way of example and not limitation, the LVP signal 310 may be obtained using a pressure sensor disposed in the left ventricle of a heart. The ECG 320 may be sensed using skin electrodes or subcutaneous electrodes under the skin. The HS signal 330 may be measured using accelerometers, microphones, or other vibrational or acoustic sensors positioned on the skin surface or implanted inside the body. As previously discussed, the HS signal may include an endocardial acceleration (EA) signal sensed by an endocranially implanted accelerometer. The conductance signal 340 may be computed as a reciprocal of the thoracic impedance, which may be measured using an impedance sensor including electrodes on the lead system 108 and the can electrode on the housing of the AMD 110. In an example, the impedance may be sensed using electrodes positioned on an epicardial surface of the heart. The conductance derivative signal 350 is computed as first derivative of the conductance signal 340, and indicates rate of change of ventricular volume. As the thoracic impedance co-varies with ventricular volume changes during systole and diastole, so does the conductance and the conductance derivative. The thoracic conductance may be proportional to ventricular volume, and the conductance derivative may be proportional to blood flow velocity inside the heart.

The P wave in the ECG 320 represents depolarization of the atria, followed by atrial contraction that extends until the QRS complex in the ECG 320 representing ventricular depolarization. The QRS marks the beginning of ventricular systole. During the ventricular systole, ventricles contract and the atrioventricular values close, creating the S1 heart sound. As the blood is propelled out of the ventricles and into the aorta and the pulmonary artery, ventricular blood volume reduces, and the impedance increases, or equivalently the conductance signal 340 decreases.

The T wave in the ECG 320 represents the repolarization of the ventricles and marks the beginning of ventricular diastole. At the beginning of ventricular diastole, ventricles relax, and semilunar values at the bases of aorta and pulmonary artery close, producing the S2 heart sound. During ventricular diastole, blood fills into the ventricles, causing a decrease in ventricular impedance, or equivalently an increase in ventricular conductance as shown in the conductance signal 340.

The ventricular diastole may include an initial rapid passive filling phase and a subsequent active filling phase. During the rapid passive filling phase, ventricular impedance decreases, or equivalently ventricular conductance increases, as indicated in an upstroke portion 341 in the conductance signal 340. The blood flow at the reduced opening of the atrioventricular septum may become turbulent until the valves are fully closed. Blood sloshing back and forth in the ventricles, or tensing of the chordate tendineae, may produce the S3 heart sound, particularly in less compliant ventricles such as due to congestive heart failure.

During the subsequent ventricular active filling phase, ventricular impedance may further decrease, or ventricular conductance further increases, as indicated in an upstroke portion 342 in the conductance signal 340, due to further blood filling into the ventricles by atrial contraction. When the atria push the blood against an abnormally stiff or hypertrophic ventricle, the S4 heart sound may be produced such as in a congestive heart failure patient.

The conductance derivative 350 may include two positive peaks 351 and 352 during the ventricular diastole. The first conductance derivative peak 351 corresponds to the upstroke portion 341 of the conductance signal 340 during the rapid passive filling phase. The second conductance derivative peak 352 corresponds to the subsequent upstroke portion 342 of the conductance signal 340 attributed to atrial contraction during the active filling phase. The conductance derivative peak 351 may temporally corresponds to the E wave observable in a Doppler echocardiograph, which represents the blood flow velocity across the mitral valve during the early diastolic filling phase. The conductance derivative peak 352 may temporally correspond to the A wave observable in a Doppler echocardiograph, which represents the blood flow velocity across the mitral valve during the late active filling phase.

FIG. 3 illustrates a temporal correspondence between HS components and the impedance or conductance characteristics in a cardiac cycle. For example, the S3 sound and the conductance derivative peak 351 both occur during the passive filling period, and the S4 sound and the conductance derivative peak 352 both occur during the active filling period. The conductance derivative peaks 351 and 352 may provide information about timing of the S3 and S4 sounds. By way of example and not limitation, the conductance derivative peak 351 may be defined as between zero-crossings 353 (going positive) and 354 (going negative). Similarly, the conductance derivative peak 352 may be defined as between zero-crossings 355 (going positive) and 356 (going negative). Temporal information of the conductance derivative peaks 351 and 352 may be used to assist HS detection, as to be discussed with reference to FIGS. 4A-D.

FIGS. 4A-D illustrate generally block diagrams of signal processor circuits 420A-D for detecting HS components, or signal metrics indicative of a cardiac diastolic function, using a HS signal and an impedance signal. The signal processor circuit 420A-D may be embodiments of the signal processor circuit 220. The impedance signal may be sensed using the impedance sensor circuit 212, and the HS signal may be sensed using the HS sensor circuit 214. Alternatively, the impedance signal or the HS signal may be received from a data storage device. The impedance signal and the HS signal may be simultaneously recorded, or time-synchronized to remove or substantially reduce the system lag and/or physiological lag between the impedance signal and the HS signal.

Figure 4A:
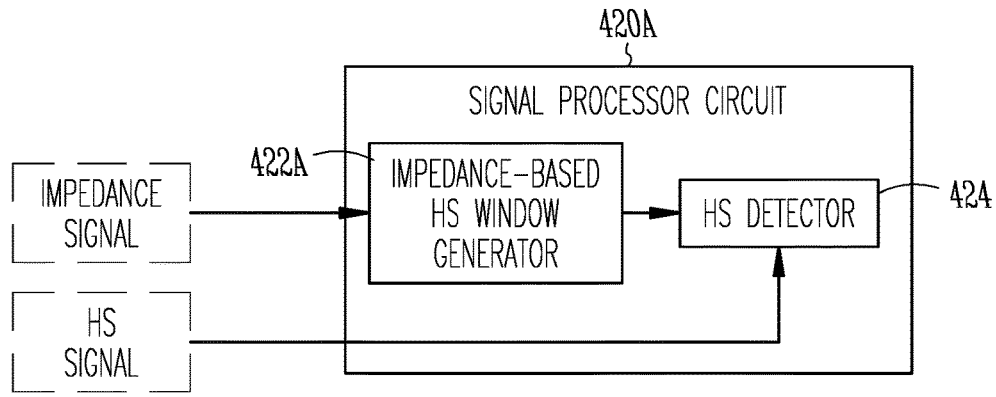
FIGS. 4A-D illustrate generally block diagrams of signal processor circuits for detecting HS components using a HS signal and an impedance signal.

In FIG. 4A, the signal processor circuit 420A may include an impedance-based HS window generator 422A configured to generate HS windows using the impedance signal, such as one or more of an S3 window $W_{S3}$ or an S4 window $W_{S4}$. The impedance-based HS window generator 422A may detect from the impedance signal a first impedance signal portion $Z_{W1}$ that temporally corresponds to a passive ventricular filling period, or a second impedance signal portion $Z_{W2}$ that temporally corresponds to an active ventricular filling period. $W_{S3}$ may be determined as a time span from the beginning to the end of the first impedance signal portion $Z_{W1}$, and $W_{S4}$ may be determined as a time span from the beginning to the end of the second impedance signal portion $Z_{W2}$. In an example, $W_{S3}$ may begin at a positive impedance peak (or equivalently a negative conductance peak) representing the beginning of diastole. $W_{S3}$ may end at a point when the impedance falls below a threshold value or when the rate of decrease in impedance (or equivalently a rate of increase in conductance) falls below a threshold representing an end of rapid passive filling period. In an example, $W_{S4}$ may begin at a deflection point of the impedance signal, subsequent to $W_{S3}$, when the impedance starts to further decrease (or when the conductance starts to further increase) representing the beginning of active filling phase. $W_{S4}$ may end at a point when the impedance falls below a threshold value, or when the rate of decrease in impedance (or equivalently the rate of increase in conductance) falls below a threshold representing an end of active filling period, or when a stimulation pulse is delivered to the heart representing a beginning of the next cardiac cycle. In some examples, $W_{S3}$ and $W_{S4}$ may be determined using the conductance derivative peaks 351 and 352 from the conductance derivative signal 350, as illustrated in FIG. 3. For example, $W_{S3}$ may be determined as between the zero-crossings 353 and 354 of the conductance derivative, and $W_{S4}$ may be determined as between the zero-crossings 355 and 356 of the conductance derivative.

The signal processor circuit 420A may include a HS detector 424 that may be configured to detect one or more HS components from the received HS signal within the determined HS detection window. For example, the HS detector 424 may detect S3 using a signal amplitude, signal energy, or other intensity measures of a portion of the HS signal within the S3 window $W_{S3}$. Similarly, the HS detector 424 may detect S4 using a signal amplitude, signal energy, or other intensity measures of a portion of the HS signal within the S4 window $W_{S4}$.

The HS detector 424 may detect one or more HS components from the received HS signal within the determined HS detection window such as produced by the impedance-based HS window generator 422A. The HS detector 424 may detect S3 or S4 using a signal amplitude, signal energy, or other intensity measures of a portion of the HS signal within the respective HS windows $W_{S3}$ or $W_{S4}$.

Figure 4B:
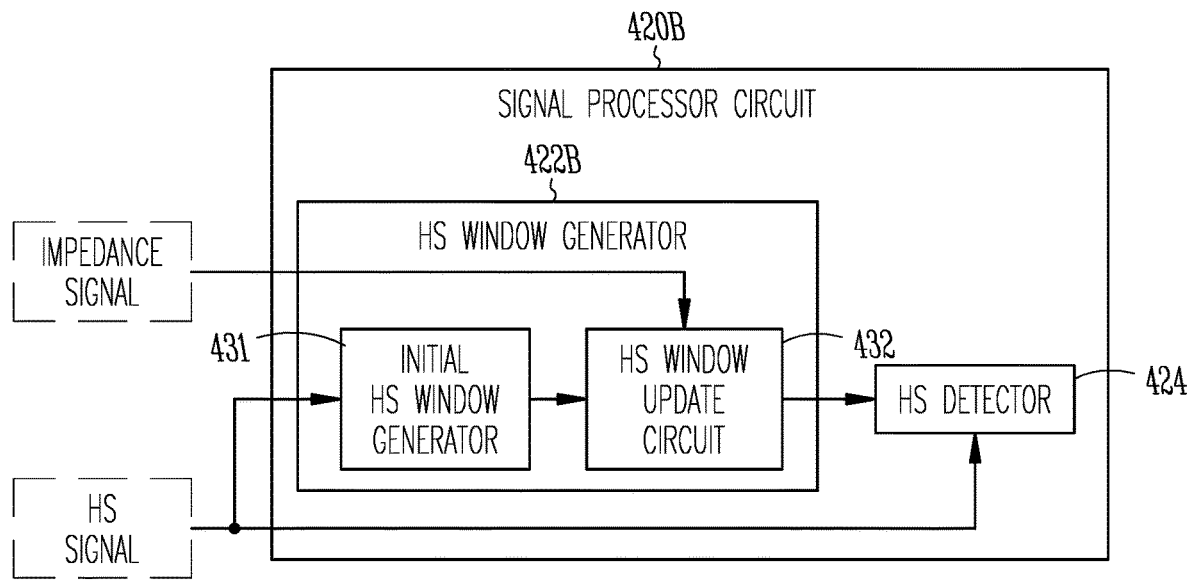
Figure 4C:
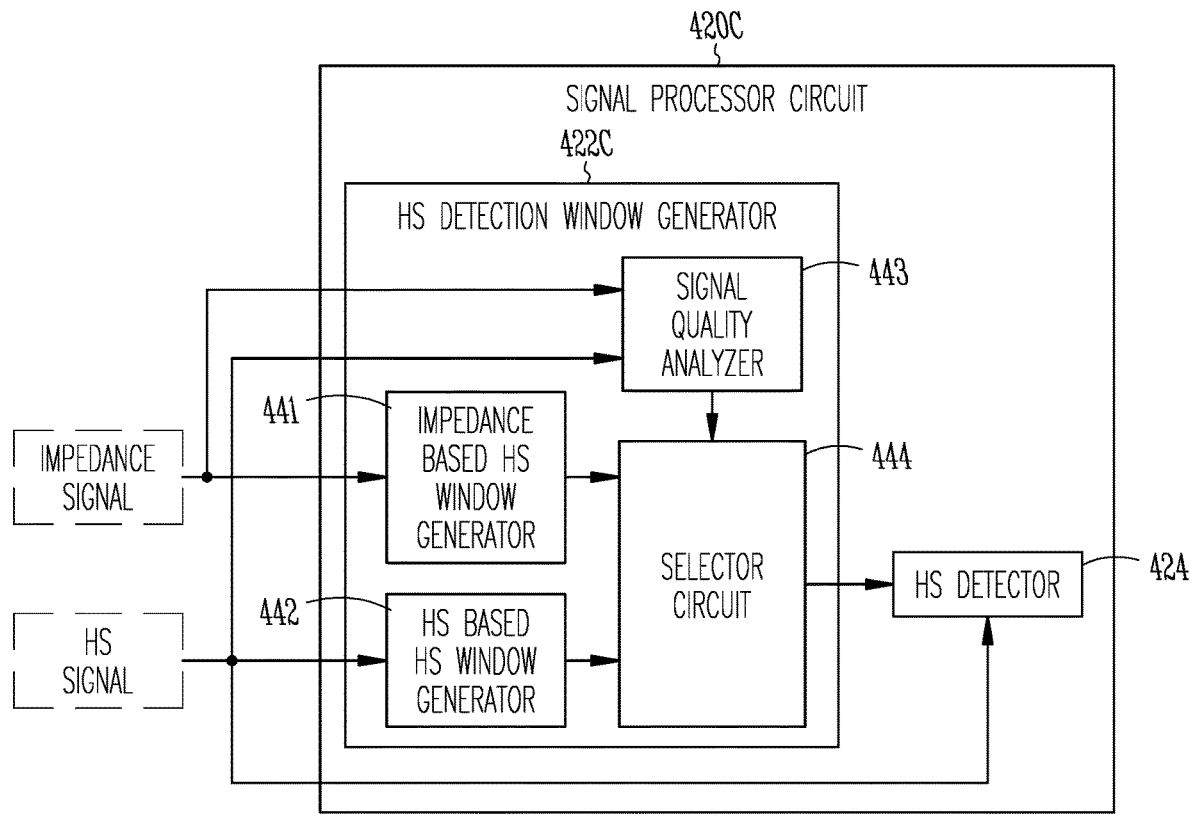

FIGS. 4B-C illustrates examples of signal processor circuits that may include respective HS window generators configured to generate HS windows, such as one or more of $W_{S3}$ or $W_{S4}$, using both the impedance signal and the HS signal. In FIG. 4B, the signal processor circuit 420B includes a HS window generator 422B that may determine the HS detection windows through a two-step process including an initial HS window determination and an update of the initial HS window. The HS window generator 422B includes an initial HS window generator 431 that may produce initial HS windows using the HS signal, such as an initial HS-based S3 window ($W_{S3\text{-}HS}$) or an initial HS-based S4 window ($W_{S4\text{-}HS}$). The initial HS-based S3 window or the S4 window may be determined using information of S1 or S2 detections. In an example, a S1 window may begin at 50 milliseconds (msec) following an R wave (or a localized ventricular depolarization) and have a duration of 300 msec. A S2 window may begin at specified offset following a detected R wave (or a localized ventricular depolarization) or S1 heart sound. An S3 window may be determined using at least one cardiac signal feature such as the R-wave timing or the timing of S2 heart sound. The S3 window may have a specified duration and may begin at a specified offset following the detected S2. In an example, the offset may be 125 msec, and the S3 window duration may be 125 msec. The offset or the S3 window duration may be a function of a physiological variable such as a heart rate. For example, the offset may be inversely proportional to the heart rate, such that the S3 detection window may start at a smaller offset following the S2 at a higher heart rate.

In an example, the initial HS window generator 431 may determine an estimate of S2 sound timing using a function of heart rate, and produce the initial HS-based windows $W_{S3\text{-}HS}$ or $W_{S4\text{-}HS}$ using the heart rate based S2 timing estimate. The S2 timing may be represented as a time delay (Q-S2) from the Q wave on an ECG to the S2 within the same cardiac cycle. Q-S2 may be empirically determined using the linear equation as follows:

$$Q\text{-}S2 = k*HR + b \qquad (1)$$

where k is the slope, and b is the intercept, of a linear regression line corresponds to various heart rates. In some examples, the initial HS window generator 431 may update a parameter of the Equation (1), such as the slope k or the intercept b, using information of patient heart sounds. The updated linear equation can provide individualized estimate of S2 timing.

The HS-based windows $W_{S3\text{-}HS}$ or $W_{S4\text{-}HS}$ may be determined using the S2 timing estimate. For example, the $W_{S3\text{-}HS}$ may begin at a specific delay from the S2 timing estimated, and $W_{S4\text{-}HS}$ may begin at a specific delay from the $W_{S3\text{-}HS}$. The HS-based windows $W_{S3\text{-}HS}$ or $W_{S4\text{-}HS}$ thus determined are related to HR, and controlled by the equation parameters k and b. The method of generating and updating the linear equation for Q-S2 timing, such as those disclosed in the commonly assigned An et al. U.S. Pat. No. 9,375,152, entitled "HEART SOUND DETECTION SYSTEMS AND METHODS USING UPDATED HEART SOUND EXPECTATION WINDOW FUNCTIONS," is hereby incorporated by reference in its entirety.

The HS window generator 422B may include a HS window update circuit 432 that may update the initial HS-based windows $W_{S3\text{-}HS}$ or $W_{S4\text{-}HS}$ using at least a portion of the impedance signal. In an example, the HS window update circuit 432 may determine an impedance-based. S3 window $W_{S3\text{-}Z}$ or an impedance-based S4 window $W_{S4\text{-}Z}$ using the slope of the impedance or conductance signal 340, or the impedance or conductance derivative signal 350, as discussed previously with reference to FIG. 3 and the impedance-based HS window generator 422A in FIG. 4A. Taking S3 window as a non-limiting example, the HS window update circuit 432 may update the initial HS-based S3 window $W_{S3\text{-}HS}$ using the impedance-based S3 window $W_{S3\text{-}Z}$. The updated S3 window, $W_{S3}$, may be computed using a combination of the $W_{S3\text{-}HS}$ and $W_{S3\text{-}Z}$, denoted by $W_{S3}=f(W_{S3\text{-}HS}, W_{S3\text{-}Z})$, where $f$ is a combination function. In an example, $f$ is an intersection operator, such that $W_{S3}$ may be determined as an intersection (i.e., an overlap) between $W_{S3\text{-}HS}$ and $W_{S3\text{-}Z}$. For example, $W_{S3}$ may begin at the later of the beginning of $W_{S3\text{-}HS}$ and the beginning of $W_{S3\text{-}Z}$, and end at the earlier of the end of $W_{S3}$ is and the end of $W_{S3\text{-}Z}$. In another example, $f$ is a union operator, such that $W_{S3}$ may be determined as a union between $W_{S3\text{-}HS}$ and $W_{S3\text{-}Z}$. For example, $W_{S3}$ may begin at the earlier of the beginning of $W_{S3\text{-}HS}$ and the beginning of $W_{S3\text{-}Z}$, and end at the later of the end of $W_{S3\text{-}HS}$ and the end of $W_{S3\text{-}Z}$. In an example, $f$ is a weighted linear operator, such that $W_{S3}$ may be determined as a weighted combination of the $W_{S3\text{-}HS}$ and $W_{S3\text{-}Z}$. For example, $W_{S3}$ may begin at some point in time between the beginning of $W_{S1\text{-}HS}$ and the beginning of $W_{S3\text{-}Z}$, and end at some point in time between the end of $W_{S3\text{-}HS}$ and the end of $W_{S3\text{-}Z}$. Other embodiments of linear or nonlinear function $f$ may also be used. The HS window update circuit 432 may similarly update the initial HS-based S4 window $W_{S4\text{-}HS}$ using the impedance-based S4 window $W_{S4\text{-}Z}$ using the combination function $f$, that is, $W_{S4\text{-}Z}=f(W_{S4\text{-}HS}, W_{S4\text{-}Z})$. The combination function for determining $W_{S4}$ may be identical to, or different from, the combination function for determining $W_{S3}$.

In an example, the HS window update circuit 432 may update the initial HS-based windows $W_{S3\text{-}HS}$ or $W_{S4\text{-}HS}$ by updating one or more equation parameters, such as k or b in Equation (1), for estimating S2 timing. As previously discussed, the HS-based S3 and S4 windows $W_{S3\text{-}HS}$ or $W_{S4\text{-}HS}$ are indirectly controlled by k or b. The HS window update circuit 432 may use the impedance-based HS windows $W_{S3\text{-}Z}$ or $W_{S4\text{-}Z}$ to calibrate Equation (1), such as by adjusting one or both of k and h until the HS-based window ($W_{S3\text{-}HS}$ or $W_{S4\text{-}HS}$) matches the impedance-based window ($W_{S3\text{-}Z}$ or $W_{S4\text{-}Z}$) within a specific margin. In an example, the beginning ($T0_{S3\text{-}HS}$) of the HS-based S3 window $W_{S3\text{-}HS}$, which may be computed as a delay from the S2 timing estimated using Equation (1), is compared to the beginning ($T0_{S3\text{-}Z}$) of the Z-based S3 window $W_{S3\text{-}Z}$. When $T0_{S3\text{-}HS}$ is within a specified margin of $T0_{S3\text{-}Z}$ (e.g., $|T0_{S3\text{-}HS}-T0_{S3\text{-}Z}|<\delta$), the calibration process may be terminated. The resulting equation parameter $k_{opt}$ and $b_{opt}$ may be used for future HS window determination.

Calibration of the linear function, such as adjustment of parameters k or b, may be performed continuously or periodically such as weekly, monthly, or at other specified periodicity. Calibration may also be automatically triggered by a trigger event such as a change in patient disease state, medical condition, exertion level, or a change of life style. In some examples, calibration may be initiated by a user command.

The HS detector 424 may detect one or more HS components from the received HS signal within the determined HS detection window such as produced by the HS window generator 422B. The HS detector 424 may detect S3 or S4 using a signal amplitude, signal energy, or other intensity measures of a portion of the HS signal within the respective HS windows $W_{S3}$ or $W_{S4}$.

In FIG. 4C, the signal processor circuit 420C includes a HS window generator 422C that may determine the HS detection using the impedance and HS signals. The HS window generator 422C includes an impedance-based HS window generator 441 and a HS-based HS window generator 442. The impedance-based HS window generator 441, which is an embodiment of the impedance-based HS window generator 422A, may detect from the impedance signal one or more HS windows such as the impedance-based S3 window $W_{S3\text{-}Z}$ and the impedance-based S4 window $W_{S4\text{-}Z}$, as discussed previously with reference to FIG. 3 and the impedance-based HS window generator 422A in FIG. 4A. The HS-based HS window generator 442 may detect HS windows using the HS signal, such as the HS-based S3 window $W_{S3\text{-}HS}$ and the HS-based S4 window $W_{S4\text{-}HS}$ determined using S2 timing estimated as a linear function of HR, as previously discussed with reference to the initial HS-based S3 window 431 in FIG. 4B. The HS window generator 422C may include a selector circuit 444 configured to select between the impedance-based HS window and the HS-based HS window. The selector circuit 444 may be coupled to a signal quality analyzer 443 that may analyze signal qualities of the impedance signal and the HS signal. In an example, the signal quality may include a signal-to-noise ratio (SNR), and the selector circuit 444 may select HS-based S3 or S4 window if the HS signal has a higher SNR than the impedance signal, or select impedance-based S3 or S4 window if the impedance signal has a higher SNR than the HS signal.

In an example, the signal quality may include a signal intensity measure, such as an amplitude or signal energy during a specific time period. For example, the signal quality analyzer 443 may determine signal energy of the impedance or conductance signal portion within the impedance-based S3 window $W_{S3\text{-}Z}$, which temporally corresponds to the passive ventricular filling period. The signal quality analyzer 443 may similarly determine signal energy of the impedance or conductance signal portion within the impedance-based S4 window $W_{S4\text{-}Z}$, which temporally corresponds to the active ventricular filling period. The selector circuit 444 may select the impedance-based S3 or S4 window if the signal energy within $W_{S3\text{-}Z}$, or the signal energy within $W_{S4\text{-}Z}$, satisfies a specific condition, such as exceeding a respective threshold. The selector circuit 444 may select the HS-based S3 or S4 window if the signal energy within $W_{S3\text{-}Z}$ or $W_{S4\text{-}Z}$ fails to satisfy the specific condition.

In an example, the signal quality may be based on information of the impedance-based E wave or A wave timing. As previously discussed, impedance or conductance derivative signal may contain characteristic signal portions (such as the peaks 351 and 352 in the conductance derivative signal 350 in FIG. 3) temporally corresponding to the E wave and the A wave in patient Doppler echocardiograph.

The signal quality analyzer 443 may receive information about E wave or A wave timing from patient echocardiograph, and compare the impedance-based E wave or A wave (e.g., the conductance derivative peaks 351 and 352) to the E wave or A wave derived from the echocardiograph. The selector circuit 444 may select the impedance-based S3 windows $W_{S3-Z}$ if the timing of the impedance-based E wave (e.g., the conductance derivative peak 351) is substantially close in time to the E wave timing from the echocardiograph within a specified margin. Similarly, the selector circuit 444 may select the impedance-based S4 windows $W_{S4-Z}$ if the timing of the impedance-based A wave (e.g., the conductance derivative peak 352) is substantially close in time to the A wave timing from the echocardiograph within a specified margin. If the impedance-based E wave or A wave (e.g., conductance derivative peaks 351 and 352) substantially differ in time from their respective counterparts of the E wave or A wave from patient echocardiograph (such as the timing difference exceeding the specified margin as discussed above), then the impedance-based E wave or A wave are deemed unreliable estimate of early passive filling phase the E wave and A wave timing. The selector circuit 444 may then select the HS-based HS windows $W_{S3-HS}$ or $W_{S4-HS}$ for HS component detection. In some examples, the information about E wave or A wave timing received by the selector circuit 444 may include empirical estimates of the E wave or A wave timing, such as respective delays relative to a reference fiducial such as a Q wave, a R wave, a T wave, a S1 sound, or a S2 sound within the same cardiac cycle. The empirical E wave and A wave timing estimates may be determined using patient population data. The selector circuit 444 may select the impedance-based HS windows $W_{S3-Z}$ or $W_{S4-Z}$ if the impedance-based E wave or A wave (e.g., the conductance derivative peaks 351 or 352) is within a specified margin of the empirical E wave and A wave timing estimates.

In an example, the signal quality may include signal sensitivity to a change in ventricular diastolic function. The change in ventricular diastolic function may include an intrinsic change of patient ventricular diastolic function, such as due to WHY in patient history. Additionally or alternatively, the change in ventricular diastolic function may be induced by electrostimulation of the heart according to different stimulation configurations, such as a change in pacing mode, pacing vector (e.g., change in at least one pacing electrode), pacing site, or a pacing parameter (e.g., pulse width, pulse amplitude, frequency, duty cycle, or stimulation duration). The signal quality analyzer 443 may detect a change in impedance signal portion, such as the ventricular conductance portions 341 and 342, or the impedance-based E wave and. A wave such as the conductance derivative peaks 351 and 352, in response to a change in cardiac electrostimulation configuration. If the signal quality analyzer 443 detects substantially concurrent (within a specified time margin) changes in the electrostimulation configuration and in the impedance-based E wave and A wave, the impedance signal may be deemed sensitive to the change in diastolic function; and the selector circuit 444 may select the impedance-based HS windows $W_{S3-Z}$ or $W_{S4-Z}$. Otherwise, the selector circuit 444 may select the HS-based HS windows $W_{S3-HS}$ or $W_{S4-HS}$ if no substantial concurrence of the changes in the electrostimulation configuration and in the impedance-based E wave and A wave is detected.

The HS detector 424 may detect one or more HS components from the received HS signal within the HS detection window such as selected by the HS window generator 422C. The HS detector 424 may detect S3 or S4 using a signal amplitude, signal energy, or other intensity measures of a portion of the HS signal within the respective HS windows $W_{S3}$ or $W_{S4}$.

Figure 4D:
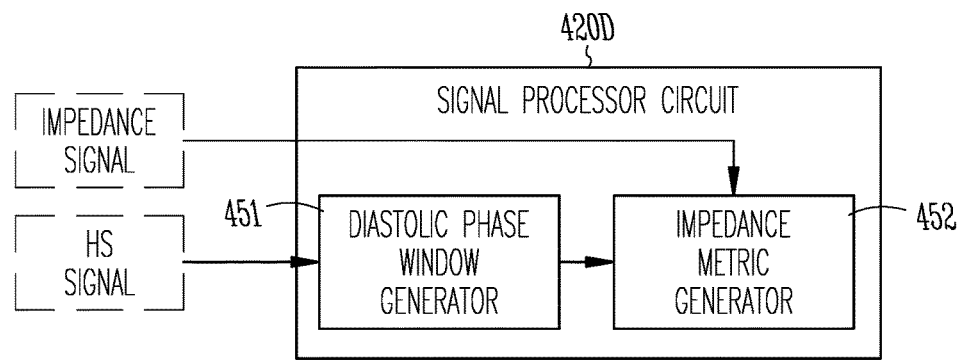

FIG. 4D illustrates a signal processor circuit 420D configured to generate impedance metrics indicative of patient ventricular diastolic function. The signal processor circuit 420D includes a diastolic phase window generator 451 and an impedance metric generator 452. The diastolic phase window generator 451 may use the received HS signal to determine a first time window corresponding to a passive ventricular filing period, and a second time window corresponding to an active ventricular filling period. In an example, the first time window may include the HS-based S3 window $W_{S3-HS}$, and the second time window may include the HS-based S4 window $W_{S4-HS}$, where the $W_{S3-HS}$ and $W_{S4-HS}$ may each be determined using an estimated S2 timing according to Equation (1), as previously discussed with reference to the initial HS-based S3 window 431 in FIG. 4B. The impedance metric generator 452 may detect a first impedance metric from a portion of the received impedance signal within the first time window, such as within $W_{S3-HS}$. The impedance metric generator 452 may similarly detect a second impedance metric from a portion of the received impedance signal within the second time window, such as within $W_{S4-HS}$. Examples of the first and second impedance metrics may each include impedance signal amplitude, signal energy, or other signal intensity measures determined within their respective first and second time windows. The impedance metrics generated by the impedance metric generator 452 may be used by the heart failure detector circuit 230 to generate DFI for detecting cardiac events such as a WHF event.

Compared to the signal processor circuit 420A which uses impedance signal to determine the time windows (e.g., $W_{S3-Z}$ and $W_{S4-Z}$) and applies the impedance-based windows to the HS signal to detect signal metrics (e.g., S3 and S4 sound intensities) that represent diastolic function, the signal processor circuit 4201) in FIG. 4D determines the time windows (e.g., $W_{S3-HS}$ and $W_{S4-HS}$) using the HS signal, and applies the HS-based windows to the impedance signal to detect a signal metric indicative of cardiac diastolic function, such as an intensity measure of a portion of the impedance signal during the passive filling period or the active filling period. The HS-based time window may be advantageous in certain patients or under certain circumstances. For example, the impedance signal may be collected via electrodes at a location vulnerable to patient physical activity or posture change. The impedance signal may be subject to interference or noise, and become less sensitive to ventricular filling during various diastolic phases. As such, the impedance-based E wave and A wave, such as the conductance derivative peaks 351 and 352 in FIG. 3, may not be reliable representation of the various diastolic phases. However, the HS signal may be less susceptible to interferences, and the HS-based windows such as $W_{S3-HS}$ and $W_{S4-HS}$ may provide more accurate and reliable estimates of the rapid passive filling period and the subsequent active filling period.

Figure 5:
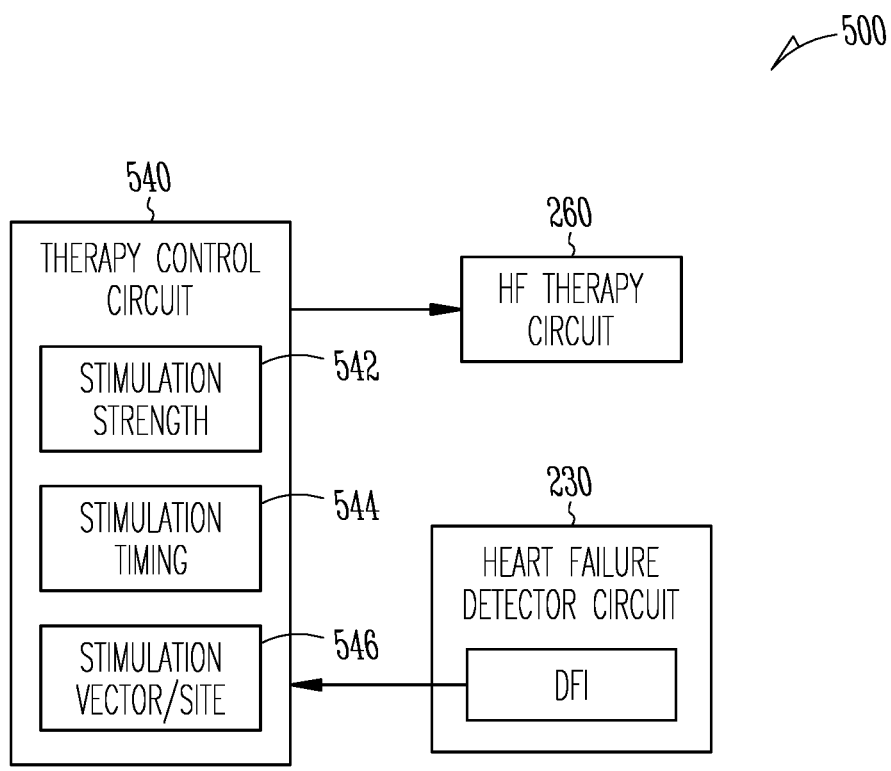
FIG. 5 illustrates generally an example of a feedback-controlled therapy delivery system.

FIG. 5 illustrates generally an example of a feedback-controlled therapy delivery system 500 configured to deliver or adjust a therapy to treat cardiac diseases such as WHF. The system 500 may be an embodiment of at least a part of the system 200. Some of all of the system 500 may be implemented in and executed by the AMD 110, distributed between two or more implantable or wearable medical devices, or distributed between the AMD 110 and the external system 125.

The system 500 may include a therapy control circuit 540, which may be a part of the controller circuit 240 of the system 200. The therapy control circuit 540 may be implemented in the external device 120, such as a programmer, and may be configured to program one or more therapy parameters. By way of example and not limitation, and as illustrated in FIG. 5, the therapy parameters may include one or more of stimulation strength parameters 542, stimulation timing parameters 544, or stimulation vector/site parameters 546, among others. Examples of the stimulation strength parameters 542 may include pulse width, pulse amplitude, frequency, duty cycle, stimulation duration, or on/off period, among others. The stimulation timing parameters 544 control the timing of stimulation pulse delivery. For example, in cardiac resynchronization therapy (CRT), the stimulation timing parameters may include an atrial-ventricular delay (AVD), a left ventricular-right ventricular delay (VVD), or a lower rate limit (LRL), among other parameters controlling the timing of delivering electrical stimulation to one or more sites of the heart. The AVD represents the latency between an intrinsically occurred atrial electrical activation signal (As) and a subsequent ventricular pacing pulse (Vp), or between an atrial pacing pulse (Ap) and the subsequent Vp. The VVD represents the latency between a left ventricular pacing pulse (LVp) and a right ventricular pacing pulse (RVp). The LRL indicates a lowest rate that a cardiac stimulation may be initiated. In another example of multisite electrostimulation of at least first and second sites of a left ventricle (LV), the stimulation parameters may include an AVD and relative timing between the stimulation of multiple LV sites. The stimulation vector/site parameters 546 may include configuration of electrostimulation vector such as designation of anode and cathode electrodes, unipolar or bipolar pacing mode, pacing site selection, location of the lead such as one of more leads within the lead system 108, among other.

The HF therapy circuit 260 may be configured to deliver heart failure therapy, such as electrostimulation of a cardiac or neural target or other tissues, according to the programmed therapy parameters. The heart failure detector circuit 230 may generate the diastolic function indicator (DFI) indicative of patient heart failure status. DFI may also indicate efficacy of the therapy such as electrostimulation therapy according to the programmed therapy parameters. Using DFI as a feedback, optionally along with other information about patient physiological responses, the therapy control circuit 540 may adjust one or more therapy parameters. The adjustment of the parameter value can be automatically performed such as by sweeping through a plurality of candidate parameter values stored in a memory circuit, or by starting with an initial candidate parameter value and then incrementally increasing or decreasing the parameter value by a specified step size. In an example, DFI may be measured in response to the ventricular pacing delivered according to the stimulation timing parameter, such as an AVD or VVD, programmed at a plurality of candidate values. The RE therapy circuit 260 may select from the plurality of candidate values a stimulation timing parameter value when the corresponding measured DFI satisfies a specific condition.

Figure 6:
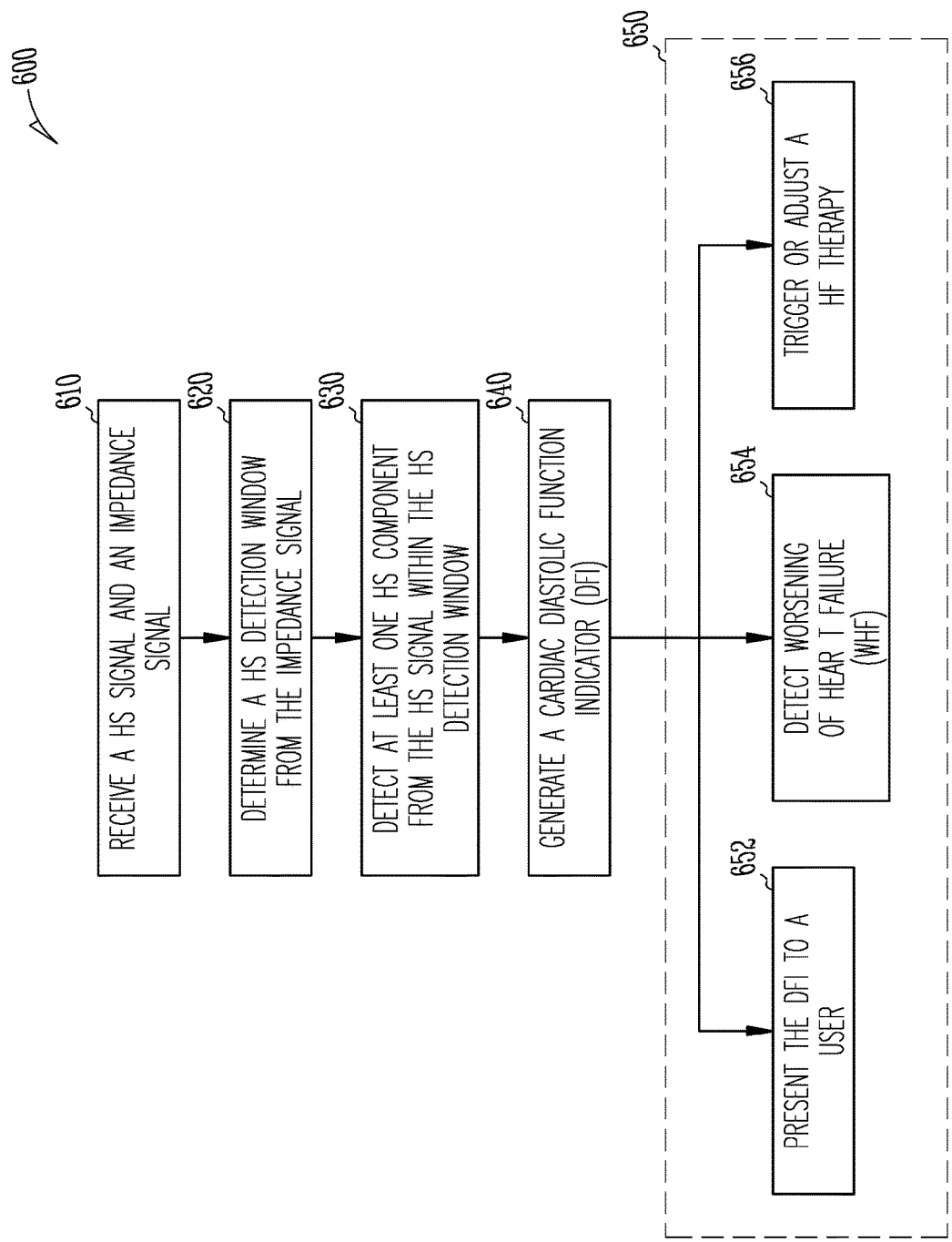
FIG. 6 illustrates generally an example of a method for monitoring cardiac function, such as a progression of a heart failure or other cardiac disease.

FIG. 6 illustrates generally an example of a method 600 for monitoring cardiac function, such as a progression of a heart failure or other cardiac disease. The method 600 may be implemented and operate in a heart failure management system, such as the cardiac monitoring system 200 in FIG. 2, or a modification thereof.

The method 600 begins at 610 by receiving physiological signals including a heart sound (HS) signal and a thoracic impedance signal sensed from a patient. The HS and impedance signals may be respectively sensed using the HS sensor circuit 214 or the impedance sensor circuit 212 as illustrated in FIG. 2. Alternatively, the HS and impedance signals sensed from the same patient may be received from a data storage device, such as an electronic medical record (EMR) system. The sensed HS signal may include one or more of HS components such S1, S2, S3 or S4. In some examples, the sensed HS signal may include an endocardial acceleration (EA) signal that similarly includes acceleration components that correspond to the S1, S2, S3, and S4 heart sounds. The impedance signal may be sensed using electrodes arranged in a bipolar, tripolar, or tetrapolar configuration. The impedance signal may represent blood volume change such as in a ventricle during different phases of a cardiac cycle. The impedance signal and the HS signals may be simultaneously sensed from the same patient, and time-synchronized to reduce the acquisition system delay and/or physiological delay between the impedance signal and the HS signal. In an example, time synchronization may be achieved by aligning the impedance signal with the HS signals using the synchronization markers.

At 620, a HS detection window may be determined using at least the sensed impedance signal. The HS detection is a time period, between a start time ($T_1$) and an end time ($T_2$), from which one or more HS components such as S1, S2, S3 or S4 may be detected. In an example, an S3 window $W_{S3}$ or an S4 window $W_{S4}$ may be determined within a cardiac cycle using the impedance signal, such as via the HS window generator 222 of the system 200. As previously discussed with reference to FIG. 3, the impedance measurement during a cardiac cycle may provide temporal information about distinctive phases of diastole, including an early passive ventricular filling period and a later active ventricular filling period. In heart failure patients with impaired diastolic function, S3 may become louder during the passive ventricular filling period, and S4 may present during the active ventricular filling period. Characteristic impedance portions from the impedance signal provides information about S3 and S4 timing, and may be used to determine the S3 window $W_{S3}$ and S4 window $W_{S4}$. Examples of the characteristic impedance portions may include the positive conductance peaks 351 and 352 during the ventricular diastole, as illustrated in FIG. 3, The conductance derivative peak 351 may be determined as between zero-crossings 353 (going positive) and 354 (going negative). The conductance derivative peak 352 may be determined as between zero-crossings 355 (going positive) and 356 (going negative). The conductance derivative peaks 351 and 352 thus determined may respectively correspond to E wave and A wave in echocardiograph, and may provide information about timing of the S3 and S4 sounds.

In some examples, in addition to the impedance signal, one or more other reference physiological signals may be used to determine the HS detection window such as the S3 window $W_{S3}$ or the S4 window $W_{S4}$, and to guide HS detection and diastolic function assessment. Examples of such reference signals may include ventricular pressure signal, ventricular wall stress, strain, or tension or force signal. In some examples, the HS detection window may be determined using the impedance signal and the HS signal. Examples of methods for determining HS windows using impedance and another physiological signal such as the HS signal are discussed below, such as with reference to FIG. 7.

At 630, at least one HS component may be detected from the sensed HS signal within the HS detection window. In an example, within a cardiac cycle, S3 may be detected from the HS signal within the S3 window, and S4 may be detected from the received HS signal within the S4 window. The detection can be made when the signal amplitude, power, or other intensity measure of the portion of the HS signal within the respective HS detection window satisfies a specified condition, such as exceeding a respective threshold value.

At 640, a cardiac diastolic function indicator (DFI) may be generated based on the detected at least one HS component. DFI may indicate diastolic dysfunction such as due to worsening heart failure (WHF). DFI may be generated using measurements from one or more of the detected S3 or S4 heart sounds. In an example, DFI may be determined using S3 intensity $\|S3\|$, S4 intensity $\|S4\|$, or a combination of $\|S3\|$ and $\|S4\|$. In a particular example, DFI may be computed using the HS intensity ratio $\|S3\|/\|S4\|$. As previously discussed with reference to FIG. 2, the HS intensity ratio $\|S3\|/\|S4\|$ may be related to the E/A ratio, a measured derived from the E wave and A wave in patient Doppler echocardiograph. S3 amplitude may be inversely proportional E wave deceleration time (DT). Both the E/A ratio and the DT are echocardiograph-based metrics for assessing diastolic function. As $\|S3\|/\|S4\|$ and $\|S3\|$ may respectively provide indirect estimates of E/A ratio and DT, DFI generated based on $\|S3\|/\|S4\|$ or $\|S3\|$ may indicate diastolic dysfunction.

In addition to or in lieu of $\|S3\|$ and $\|S4\|$ or a combination thereof, other HS signal metrics generated from the detected S3 or S4 heart sounds may be used to determine DFI at 640. Examples of such HS signal metrics may include a slope of S3 peak within the S3 detection window, a slope of S4 peak within the S4 detection window, a frequency of the HS signal portion within the S3 detection window, or a frequency of the signal portion within the S4 detection window, or a combination of two or more of these HS signal metrics.

In some examples, at 640, DFI may be generated using impedance metrics in addition to, or in lieu of, the HS component detected at 630. The impedance metrics may be generated from the sensed impedance signal within a HS-based S3 window $W_{S3-HS}$ corresponding to a passive ventricular filing period, or a HS-based S4 window $W_{S4-HS}$ corresponding to an active ventricular filling period, such as via the signal processor circuit 420D as illustrated in FIG. 4D. A first impedance metric may be generated from a portion of the received impedance signal within $W_{S3-H}$. A second impedance metric may be generated from a portion of the received impedance signal within $W_{S4-HS}$. Examples of the first and second impedance metrics may each include impedance signal amplitude, signal energy, or other signal intensity measures determined within their respective first and second time windows. The process of generating DFI using the first and second impedance metrics, as discussed herein, is an alternative to steps 620 and 630. While steps 620 and 630 involves time windows (e.g., $W_{S3-Z}$ and $W_{S4-Z}$) determined using the impedance signal and subsequently and subsequent application to the HS signal to determine the signal metrics (e.g., S3 and S4 sound intensities) for generating DFI, the alternative process involves time windows (e.g., $W_{S3-HS}$ and $W_{S4-HS}$) determined using the HS signal and subsequent application to the impedance signal to detect signal metrics (e.g., impedance signal intensities during the respective windows $W_{S3-HS}$ and $W_{S4-HS}$) for generating DFI.

At 650, DFI may be output to a user or a processor. In an example, at 652, DPI may be presented to a user, such as via a display at the user interface 250 in FIG. 2. A human-perceptible presentation of DEL optionally along with other information such as the HS and impedance signals, HS detection windows and detected HS components (e.g., S3 and S4), may be displayed in a user-interface. Additionally or alternatively, at 654, worsening heart failure (WHF) may be detected using DFI. In an example, DFI may be computed and trended over time, and WHF is detected if the trended DPI exceeds a respective threshold or falls within a respective region. Additionally or alternatively, at 656A, a heart failure therapy may be recommended or delivered to the patient based on DFI or the detection of WHF. The therapy may include electrostimulation therapy delivered a cardiac tissue, a nerve tissue, or other target tissues, or drug therapy including delivering drug to a tissue or organ. In an example, the electrostimulation therapy may include cardiac pacing therapy from a region inside a heart chamber or on the epicardial surface of the heart, such as a cardiac resynchronization therapy (CRT), or multi-site pacing at a heart chamber such as a left ventricle.

In some examples, one or more therapy control parameters may be adjusted, such as via the feedback-controlled therapy system 500 as illustrated in FIG. 5, when DPI satisfies a specific condition. The adjustment of therapy may include adjusting one or more stimulation strength parameters, stimulation timing parameters, or inter-stimulation or stimulation vector/site parameters. In an example, one or more of an atrial-ventricular delay (AVD), a left ventricular-right ventricular delay (VVD), a lower rate limit (LRL), among other stimulation timing parameters, may be adjusted when DFI falls below a threshold or within a specified range indicating undesirable efficacy of an existing therapy. The adjustment of the parameter value can be automatically performed such as by sweeping through a plurality of candidate parameter values stored in a memory circuit, or by starting with an initial candidate parameter value and then incrementally increasing or decreasing the parameter value by a specified step size. DFI may be measured in response to the ventricular pacing delivered according to the adjusted stimulation timing parameter, and desired values of the stimulation timing parameter may be determined when the corresponding stimulation results in a DEI that satisfies a specified condition, such as exceeding a threshold or higher than DFIs resulted from stimulation according to at least some other values of the simulation timing parameters.

Figure 7:
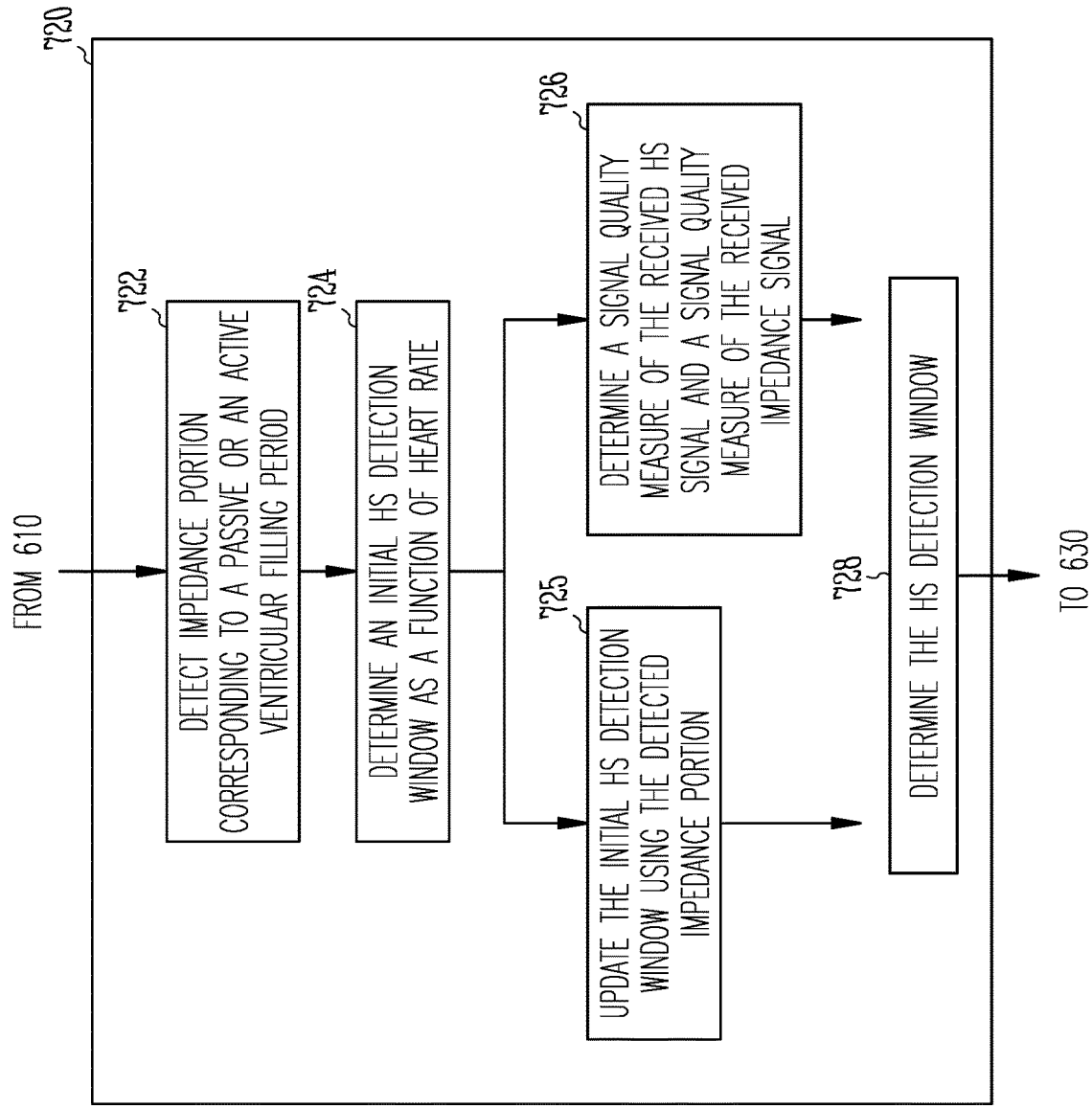
FIG. 7 illustrates generally an example of a method for determining a HS detection window using at least an impedance signal.

FIG. 7 illustrates generally an example of a method 720 for determining a HS detection window using at least an impedance signal. The method 720, which may be an embodiment of the step 620 in FIG. 6, may be implemented in and executed by one of the window generators 422A-C, as illustrate in FIGS. 4A-C.

At 722, an impedance portion corresponding to a passive or an active ventricular filling period may be determined from the sensed impedance signal received at 720, such as via the impedance-based HS window generator 422A in FIG. 4A, or the impedance-based HS window generator 441 in FIG. 4C. The impedance portion may include a first impedance portion $Z_{W1}$ temporally corresponding passive ventricular filling period, or a second impedance portion $Z_{W2}$ temporally corresponding to an active ventricular filling period. In an example, the first and second impedance portions $Z_{W1}$ and $Z_{W2}$ may be determined as impedance-based E wave and A wave shown as the conductance derivative peaks 351 and 352. An impedance-based S3 window $W_{S3-Z}$ may be determined as a time span from the beginning to the end of the first impedance portion $Z_{W1}$, and an impedance-based S4 window $W_{S4-Z}$ may be determined as a time span from the beginning to the end of the second impedance signal portion $Z_{W2}$. For example, $W_{S3}$ may be determined as between the zero-crossings 353 and 354 of the conductance derivative, and $W_{S4}$ may be determined as between the zero-crossings 355 and 356 of the conductance derivative.

At 724, an initial HS detection window may be determined from the HS signal received from 610, such as via the initial HS window generator 431 in FIG. 4B or the HS-based HS window generator 442 in FIG. 4C. The initial Hs window, such as HS-based S3 or S4 window $W_{S3-HS}$ or $W_{S4-HS}$, may be determined using information of S1 or S2 detections. In an example, the S2 timing, such as Q-S2 timing, may be estimated using a linear function of heart rate, Q-S2=k*HR+h, where k is the slope, and b is the intercept, of a linear regression line corresponds to various heart rates. The initial HS-based windows $W_{S3-HS}$ or $W_{S4-HS}$ may be determined using the heart rate based S2 timing estimate. For example, the $W_{S3-HS}$ may begin at a specific delay from the S2 timing estimated, and $W_{S4-HS}$ may begin at a specific delay from the $W_{S3-HS}$. The HS-based windows $W_{S3-HS}$ or $W_{S4-HS}$ thus determined are related to HR, and controlled by the equation parameters k and b.

The impedance signal portions detected from 722 and the initial HS detection window determined at 724 may then be combined to determine an estimate of the HS window, such as one or more of $W_{S3}$ or $W_{S4}$. By way of example and not limitation, the combination may through one or both of the steps 725 and 726. At 725, the initial HS detection window as determined from step 724 may be updated using information extracted from the detected impedance portion as detected from 722, such as via the HS window update circuit 432 as illustrated in FIG. 4B. In an example, the impedance-based S3 window $W_{S3-Z}$, representing the time span of the impedance portion corresponding to the passive filling period as determined as 722, may be used to update the initial HS-based S3 window $W_{S3-HS}$. In a similar fashion, the impedance-based S4 window $W_{S4-Z}$, representing the time span of the impedance portion corresponding to the subsequent active filling period, may be used to update the initial HS-based S4 window $W_{S4-HS}$. Taking the update of $W_{S3-HS}$ as an example, the update process may involve a computation of an intersection (i.e., an overlap) between the $W_{S3-HS}$ and $W_{S3-Z}$, such that the updated S3 window, $W_{S3}$, may begin at the later of the beginning of $W_{S3-S}$ and the beginning of $W_{S3-Z}$, and end at the earlier of end of $W_{S3-HS}$ and the end of $W_{S3-Z}$. In another example, the update process may involve a computation of a union between the $W_{S3-HS}$ and $W_{S3-Z}$, such that the updated S3 window $W_{S3}$ may begin at the earlier of the beginning of $W_{S3-HS}$ is and the beginning of $W_{S3-Z}$, and end at the later of end of $W_{S3-HS}$ and the end of $W_{S3-Z}$. In an example, the update may include weighted combination between the $W_{S3-HS}$ and $W_{S3-Z}$. For example, $W_{S3}$ may begin at an average of, or a specified time between, the beginning of $W_{S3-HS}$ and the beginning of $W_{S3-Z}$, and end at an average of, or a specified time between, the end of $W_{S3-HS}$ and the end of $W_{S3-Z}$. In yet another example, when the HS-based S3 window $W_{S3-HS}$ is determined based on S2 timing estimated using a linear function (1), the update may involve an update of one or more function parameters such that the slope k or the intercept b until the HS-based S3 window $W_{S3-HS}$ or the S4 window or $W_{S4-HS}$ matches the impedance-based S3 window $W_{S3-Z}$ or the S4 window or $W_{S4-Z}$ within a specific tolerance. The updated HS detection window may be determined at 728 as the HS detection window for use to detect HS components such as S3 and S4 at 630.

As an alternative to or in lieu of detection window update at 725 using the information from the detected impedance portion, at 726, a signal quality measure of the received HS signal and a signal quality measure of the received impedance signal may be determined, such as via the signal quality analyzer 443 in FIG. 4C. In an example, the signal quality may include a signal-to-noise ratio (SNR). The HS-based S3 or S4 window may be selected at 728 as the HS window if the HS signal has a higher SNR than the impedance signal, or the impedance-based S3 or S4 window may be selected at 728 as the HS window if the impedance signal has a higher SNR than the HS signal. In another example, the signal quality may include a signal intensity, such as an amplitude or signal energy measurement during a specific time period. At 728, the impedance-based S3 or S4 window may be selected as the HS detection windows if the signal energy within $W_{S3-Z}$, or the signal energy within $W_{S4-Z}$, exceeds a specified threshold. Otherwise, the HS-based S3 or S4 window are selected. In an example, the signal quality may include an assessment of reliability of the impedance-based E wave and A wave estimates, such as conductance derivative peaks 351 and 352, in representing the echocardiograph-based E wave or A wave timing. The impedance-based HS windows $W_{S3-Z}$ or $W_{S4-Z}$ may be selected as the HS detection window at 728 if the detected conductance derivative peak 351 is within a specified margin of the received E wave timing, or the detected conductance derivative peak 352 is within a specified margin of the received A wave timing. Otherwise, the HS-based HS windows $W_{S3-HS}$ or $W_{S4-HS}$ are instead selected at 728. In yet another example, the signal quality may include signal sensitivity to a change in ventricular diastolic function such as induced by changing cardiac electrostimulation configuration. For example, the impedance-based E wave and A wave, shown as the conductance derivative peaks 351 and 352, may be detected in response to a change in pacing mode, pacing vector (including a change in pacing electrode), pacing site, or a pacing strength or duration parameter cardiac electrostimulation configuration. If the impedance-based E wave and A wave concurrently change with the changes in electrostimulation configuration, then the impedance signal is deemed sensitive to the change in diastolic function, and the impedance-based HS windows $W_{S3-Z}$ or $W_{S4-Z}$ may be selected at 728. Otherwise, the HS-based HS windows $W_{S3-HS}$ or $W_{S1-HS}$ are instead selected for detecting HS components at 630.

Figure 8:
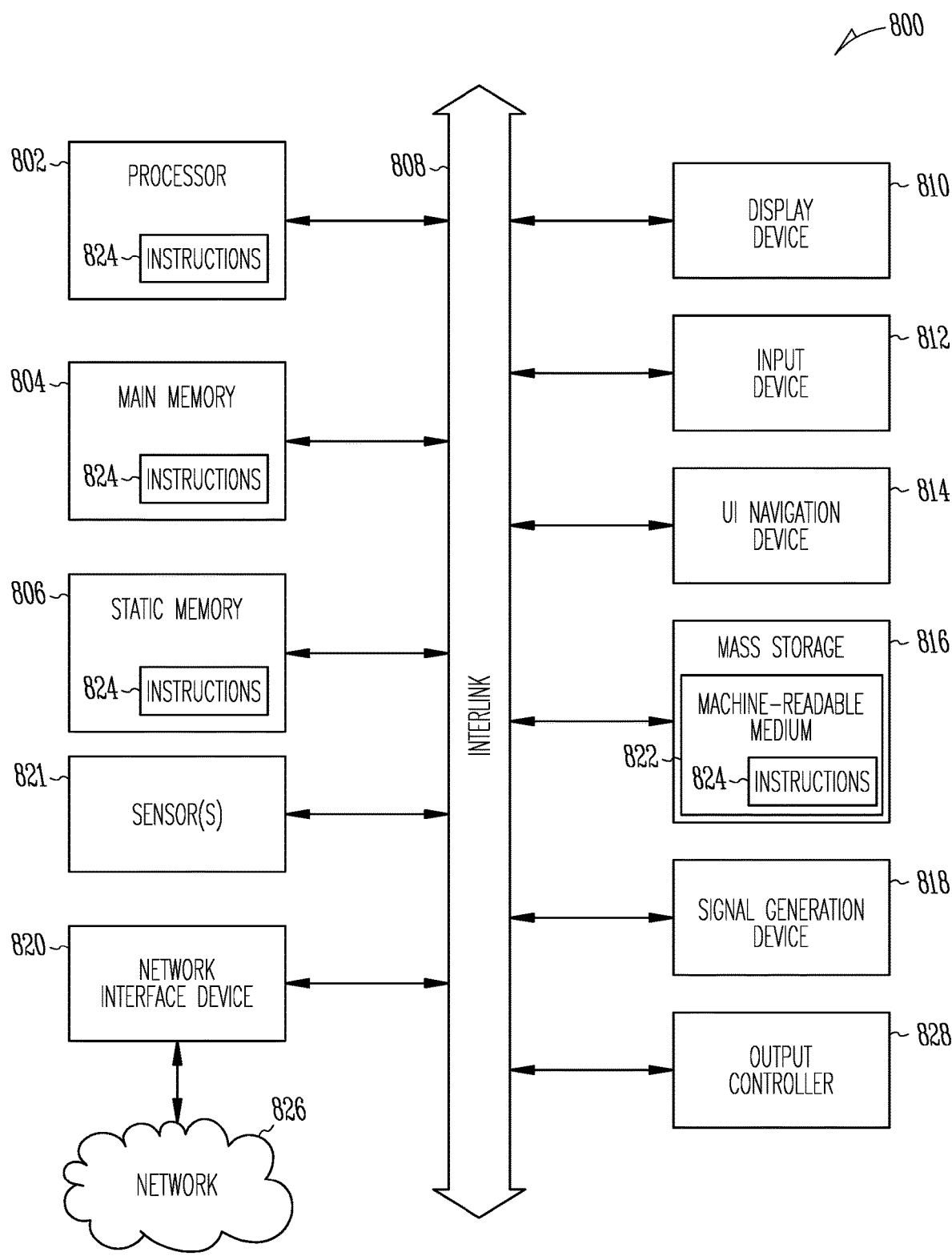
FIG. 8 illustrates generally a block diagram of an example machine upon which any one or more of the techniques (e.g., methodologies) discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples, An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for managing heart failure in a patient, the system comprising:
   a signal receiver circuit configured to receive a heart sound (HS) signal and an impedance signal sensed from the patient;
   a heart sound detector circuit configured to:
      determine a HS detection window for detecting at least one of a third heart sound (S3) component or a fourth heart sound (S4) component using values from the received impedance signal; and
      detect at least one of the S3 component or the S4 component from the received HS signal within the determined HS detection window; and
   a heart failure detector circuit configured to generate a cardiac diastolic function indicator (DFI) using the detected at least one of the S3 component or the S4 component.

2. The system of claim 1, wherein the heart sound detector circuit is configured to:
   detect, from the received impedance signal, an impedance portion temporally corresponding to a passive ventricular filling period or an active ventricular filling period; and
   determine the HS detection window using the detected impedance portion.

3. The system of claim 2, wherein the heart sound detector circuit is configured to:
   determine, from the received HS signal, an initial HS detection window as a function of heart rate;
   adjust a parameter of the function using information extracted from the detected impedance portion; and
   determine the HS detection window using the function with the adjusted parameter.

4. The system of claim 2, wherein the heart sound detector circuit is configured to:
   determine a signal quality measure of the received HS signal and a signal quality measure of the received impedance signal; and
   select between the initial HS detection window and the detected impedance portion to determine the HS detection window based on the signal quality measure of the received HS signal and the signal quality measure of the received impedance signal.

5. The system of claim 4, wherein the signal quality measure of the received impedance signal includes a signal strength of the detected impedance portion temporally corresponding to a passive ventricular filling period or an active ventricular filling period.

6. The system of claim 4, wherein the signal quality measure of the received impedance signal includes a sensitivity of the detected impedance portion to cardiac electrostimulation according to at least two different stimulation configuration.

7. The system of claim 1, wherein the heart failure detector circuit is configured to detect worsening heart failure using the DFI,
   the system comprising a therapy circuit configured to deliver or adjust a therapy when the generated DFI satisfies a specific condition.

8. The system of claim 7, wherein the therapy includes cardiac electrostimulation, and the therapy circuit is configured to:
   adjust a stimulation timing parameter using the DFI; and
   deliver the cardiac electrostimulation according to the adjusted stimulation timing parameter.

9. The system of claim 8, wherein the stimulation timing parameter includes an atrio-ventricular delay (AVD) or interventricular delay (VVD) with respect to a reference event for initiating a ventricular pacing therapy, and the therapy circuit is configured to determine the stimulation timing parameter, including:
   measure the DFI in response to the ventricular pacing delivered according to the stimulation timing parameter programmed at a plurality of candidate values; and
   select from the plurality of candidate values a stimulation timing parameter value when the corresponding measured DFI satisfies a specific condition.

10. The system of claim 1, wherein the heart sound detector circuit is configured to:
    determine an S3 detection window and an S4 detection window using the received impedance signal; and
    detect S3 from the received HS signal within the S3 detection window and detect S4 from the received HS signal within the S4 detection window.

11. The system of claim 10, wherein the heart failure detector circuit is configured to generate the DFI using a ratio of an intensity of the detected S3 to an intensity of the detected S4.

12. A method for managing heart failure in a patient using a medical system, the method comprising:
    receiving, via a signal receiver circuit, a heart sound (HS) signal and an impedance signal sensed from the patient;
    determining, via a heart sound detector circuit, a HS detection window for detecting at least one of a third heart sound (S3) component or a fourth heart sound (S4) component from values of the received impedance signal;
    detecting, via the heart sound detector circuit, at least one of the S3 component or the S4 component from the received HS signal within the determined HS detection window; and
    generate, via the heart failure detector circuit, a cardiac diastolic function indicator (DFI) using the detected at least one of the S3 component or the S4 component.

13. The method of claim 12, wherein determining the HS detection window from the received impedance signal includes:
    detecting, from the received impedance signal, an impedance portion temporally corresponding to a passive ventricular filling period or an active ventricular filling period; and
    determining the HS detection window using the detected impedance portion.

14. The method of claim 13, wherein determining the HS detection window from the received impedance signal includes:
    determining from the received HS signal an initial HS detection window as a function of heart rate;
    adjusting a parameter of the function using information extracted from the detected impedance portion; and determining the HS detection window using the function with the adjusted parameter.

15. The method of claim 13, wherein determining the HS detection window from the received impedance signal includes:
   determining a signal quality measure of the received HS signal and a signal quality measure of the received impedance signal; and
   selecting between the initial HS detection window and the detected impedance portion to determine the HS detection window based on the signal quality measure of the received HS signal and the signal quality measure of the received impedance signal.

16. The method of claim 15, wherein the signal quality measure of the received impedance signal includes at least one of:
   a signal strength of the detected impedance portion temporally corresponding to a passive ventricular filling period or an active ventricular filling period; or
   a sensitivity of the detected impedance portion to cardiac electrostimulation according to at least two different stimulation configuration.

17. The method of claim 12, comprising:
   determining, from the received impedance signal, an S3 detection window and an S4 detection window using the received impedance signal;
   detecting S3 from the received HS signal within the S3 detection window and detecting S4 from the received HS signal within the S4 detection window; and
   generating the DFI using a ratio of an intensity of the detected S3 to an intensity of the detected S4.

18. The method of claim 12, comprising detecting worsening heart failure using the generated DFI and delivering or adjusting a therapy when the generated DFI satisfies a specific condition.

19. A system for managing heart failure in a patient, comprising:
   a signal receiver configured to receive a heart sound (HS) signal and an impedance signal sensed from the patient;
   a heart sound detector circuit configured to:
      detect, from the received impedance signal, a first impedance portion temporally corresponding to a passive ventricular filling period, and a second impedance portion temporally corresponding to an active ventricular filling period;
      determine a third heart sound (S3) detection window using the first impedance portion and a fourth heart sound (S4) detection window using the second impedance portion; and
      detect S3 from the received HS signal within the S3 detection window, and detect S4 from the received HS signal within the S4 detection window;
   a heart failure detector circuit configured to generate a cardiac diastolic function indicator (DFI) using a ratio of an intensity of the detected S3 to an intensity of the detected S4; and
   a therapy circuit configured to determine a stimulation timing parameter using the DFI, and deliver cardiac electrostimulation according to the determined stimulation timing parameter.

20. The system of claim 19, wherein the heart sound detector circuit is configured to:
   detect, from the received HS signal, a second heart sound (S2) timing using a linear function of heart rate;
   adjust a parameter of the linear function using information extracted from the first or second impedance portion; and
   determine at least one of the S3 detection window or the S4 detection window based on a S2 timing estimated using the linear function with the adjusted parameter.

* * * * *